(12) United States Patent
Jin et al.

(10) Patent No.: US 9,206,402 B2
(45) Date of Patent: Dec. 8, 2015

(54) COMPOSITION AND FORMULATION COMPRISING RECOMBINANT HUMAN IDURONATE-2-SULFATASE AND PREPARATION METHOD THEREOF

(75) Inventors: Thong-Gyu Jin, Seoul (KR); Yo Kyung Chung, Yongin-si (KR); Sang Hoon Paik, Yongin-si (KR); Yoo Chang Park, Yongin-si (KR); Jinwook Seo, Yongin-si (KR); Yong Woon Choi, Yongin-si (KR); Jong Mun Son, Yongin-si (KR); Yong-Chul Kim, Yongin-si (KR)

(73) Assignees: GREEN CROSS CORPORATION, Yongin-si (KR); MediGeneBio Corporation, Yongin-si (KR)

( * ) Notice: Subject to any disclaimer, the term of this patent is extended or adjusted under 35 U.S.C. 154(b) by 164 days.

(21) Appl. No.: 14/128,918

(22) PCT Filed: Jun. 15, 2012

(86) PCT No.: PCT/KR2012/004734
§ 371 (c)(1),
(2), (4) Date: Dec. 23, 2013

(87) PCT Pub. No.: WO2012/177020
PCT Pub. Date: Dec. 27, 2012

(65) Prior Publication Data
US 2014/0242059 A1    Aug. 28, 2014

Related U.S. Application Data

(60) Provisional application No. 61/500,994, filed on Jun. 24, 2011.

(30) Foreign Application Priority Data

Feb. 8, 2012    (KR) .................... 10-2012-0012718

(51) Int. Cl.
*C12N 9/16* (2006.01)
*A61K 38/46* (2006.01)

(52) U.S. Cl.
CPC ............... *C12N 9/16* (2013.01); *A61K 38/465* (2013.01); *C12Y 301/06013* (2013.01)

(58) Field of Classification Search
CPC ..................... A61K 38/465; C12Y 301/06013
USPC ........................................... 435/196; 424/94.6
See application file for complete search history.

(56) References Cited

U.S. PATENT DOCUMENTS

| | | | |
|---|---|---|---|
| 6,153,188 | A | 11/2000 | Wilson et al. |
| 9,051,556 | B2 | 6/2015 | Nichols |
| 2004/0229250 | A1 | 11/2004 | Figura et al. |

FOREIGN PATENT DOCUMENTS

WO    2005113765 A2    12/2005

OTHER PUBLICATIONS iduronate 2-sulfatase isoform a precursor [Homo sapiens], NCBI Reference Sequence: NP_000193.1, May 14, 2011, 3 pages total.
Muenzer, Joseph et al., "A phase II/III clinical study of enzyme replacement therapy with idursulfase in mucopolysaccharidosis II (Hunter syndrome)", Genetics in Medicine, vol. 8, No. 8, pp. 465-473, (2006).
State Intellectual Property Office of People'S Republic of China, Communication dated Aug. 27, 2014, issued in corresponding Chinese application No. 201280030629.X.
Bielicki, "Recombinant human iduronate-2-sulphatase: correction of mucopolysaccharidosis-type II fibroblasts and characterization of purified enzyme", Biochemical Journal, vol. 289, Jan. 1, 1993, pp. 241-246, XP055081180, GB ISSN: 0264-6021.
Fraldi A et al.., "SUMF1 enhances sulfatase activities in vivo in five sulfatase deficiencies", Biochemical Journal, Portland Press Ltd., GB, vol. 403, No. 2, Apr. 15, 2007, pp. 305-312, XP002601852, ISSN: 0264-6021.
Chung et al., "A biochemical and physicochemical comparison of two recombinant enzymes used for enzyme replacement therapies of hunter syndrome", Glycoconjugate Journal, vol. 31, No. 4, Apr. 30, 2014, pp. 309-315, XP55149968, ISSN: 0282-0080.
European Patent Office, Communication dated Nov. 20, 2014, issued in corresponding European Application No. 12803297.6.
Australian Patent Office, Communication dated Apr. 1, 2015 in counterpart application No. 2012274215.
Muenzer, J. et al. 'A Phase I/II Clinical Trial of Enzyme Replacement Therapy in Mucopolysaccharidosis II (Hunter Syndrome)', Molecular Genetics and Metabolism, 2007, vol. 90 pp. 329-337.
Sohn et al. "Phase I/II clinical trial of enzyme replacement therapy with idursulfase beta in patients with mucopolysaccharidosis II (Hunter Syndrome)", Orphanet Journal of Rare Diseases , Mar. 18, 2013, 8:42. pp. 1-8.
Chung et al. "A biochemical and physiochemical comparison of two recombinant enzymes used for enzyme replacement therapies of hunter syndrome", Glycoconj J (2014) 31: pp. 309-315.
Cho et al. "Impact of Enzyme Replacement Therapy on Linear Growth in Korean Patients with Mucopolysaccharidosis Type II (Hunter Syndrome)", J Korean Med Sci. (2014); 29: pp. 254-260.
Sohn et al. "Safety and efficacy of enzyme replacement therapy with idursulfase beta in children aged younger than 6 years with Hunter syndrome", Molecular Genetics and Metabolism, Aug. 6, 2014; pp. 1-5.

*Primary Examiner* — Tekchand Saidha
(74) *Attorney, Agent, or Firm* — Sughrue Mion, PLLC

(57) ABSTRACT

Disclosed is a composition comprising recombinant iduronate-2-sulfatase (IDS). The glycosylation pattern and formylglycine content of the IDS composition are different from those of Elaprase and have superior pharmaceutical efficacy and are safer than the conventional agent and thus can be effectively used for the therapy of Hunter syndrome.

24 Claims, 18 Drawing Sheets

Lane M: Protein size marker
Lane 1: glycosylated IDS
Lane 2: IDS treated with PNGase
Lane 3: deglycosylated IDS

FIG. 6

| | | | | |
|---|---|---|---|---|
| 10 | 20 | 30 | 40 | 50 |
| SETQANSTTD | ALNVLLIIVD | DLRPSLGCYG | DKLVRSPNID | QLASHSLLFQ |
| 60 | 70 | 80 | 90 | 100 |
| NAFAQQAVCA | PSRVSFLTGR | RPDTTRLYDF | NSYWRVHAGN | FSTIPQYFKE |
| 110 | 120 | 130 | 140 | 150 |
| NGYVTMSVGK | VFHPGISSNH | TDDSPYSWSF | PPYHPSSEKY | ENTKTCRGPD |
| 160 | 170 | 180 | 190 | 200 |
| GELHANLLCP | VDVLDVPEGT | LPDKQSTEQA | IQLLEKMKTS | ASPFFLAVGY |
| 210 | 220 | 230 | 240 | 250 |
| HKPHIPFRYP | KEFQKLYPLE | NITLAPDPEV | PDGLPPVAYN | PWMDIRQRED |
| 260 | 270 | 280 | 290 | 300 |
| VQALNISVPY | GPIPVDFQRK | IRQSYFASVS | YLDTQVGRLL | SALDDLQLAN |
| 310 | 320 | 330 | 340 | 350 |
| STIIAFTSDH | GWALGEHGEW | AKYSNFDVAT | HVPLIFYVPG | RTASLPEAGE |
| 360 | 370 | 380 | 390 | 400 |
| KLFPYLDPFD | SASQLMEPGR | QSMDLVELVS | LFPTLAGLAG | LQVPPRCPVP |
| 410 | 420 | 430 | 440 | 450 |
| SFHVELCREG | KNLLKHFRFR | DLEEDPYLPG | NPRELIAYSQ | YPRPSDIPQW |
| 460 | 470 | 480 | 490 | 500 |
| NSDKPSLKDI | KIMGYSIRTI | DYRYTVWVGF | NPDEFLANFS | DIHAGELYFV |
| 510 | 520 | 530 | | |
| DSDPLQDHNM | YNDSQGGDLF | QLLMP | | |

FIG. 10

|  |  | 10 |  |  | 30 |  | 50 |  |
|--|--|--|--|--|--|--|--|--|
| SETQA | ALAUL | NSTID | LIIUD | DLRPS | LCCYG | DKLUR | SPNID | QLASH | SLLFQ | NAFAQ | QAUCA |
| | | 70 | | | 90 | | | 110 | | | |
| PSRUS | FLIGR | RPDTT | RLYDF | NSYWR | UHAGN | FSTIP | QYFKE | NGYUT | MSUGK | UFHPG | ISSNH |
| | | 130 | | | 150 | | | 170 | | | |
| TDDSP | YSUSF | PPYHP | SSEKY | ENTKT | CRGPD | GELHA | NLLCP | UDULD | UPEGT | LPDKQ | STEQA |
| | | 190 | | | 210 | | | 230 | | | |
| IQLLE | KMKTS | ASPFF | LAUGY | HKPHI | PPRYP | KEFQK | LYPLE | NITLA | PDPEU | PDGLP | PUAYN |
| | | 250 | | | 270 | | | 290 | | | |
| PWMDI | RQRED | UQRLM | ISUPY | GPIPU | DFQRK | IRQSY | FASUS | YLDTQ | UGRLL | SALDD | LQLAN |
| | | 310 | | | 330 | | | 350 | | | |
| STIIA | FTSDH | GMRLG | EHGEU | AKYSN | FDUAT | HUPLI | FYUPG | RTASL | PEAGE | XLPPY | LDPFD |
| | | 370 | | | 390 | | | 410 | | | |
| SASQL | MEPGR | QSMDL | UELUS | LPPTL | AGLAG | LQUPP | RCPUP | SFHUE | LCREG | XMLLX | HFRFR |
| | | 430 | | | 450 | | | 470 | | | |
| DLEED | PYLPG | NPREL | IAYSQ | YPRPS | DIPQW | NSDXP | SLKDI | KINGY | SIRTI | DYRYT | UWUGF |
| | | 490 | | | 510 | | | | | | |
| NPDEP | LANFS | DIHAG | ELYPU | DSDPL | QDHNM | UNDSQ | GGDLP | QLLMA | | | |

Lane 1, 8: Molecular size marker
Lane 2: IDS
Lane 3: IDS treated with PNGase F
Lane 4: IDS treated with Endo H
Lane 5: IDS treated with O-glycosidase
Lane 6: IDS treated with Sialidase
Lane 7: IDS treated with PNGase F and O-glycosidase Lane M: size marker
Lane 1: a loaded sample for cation exchange chromatography
Lane 2: an eluate of cation exchange chromatography
Lane 3: a regeneration solution after cation exchange chromatography

SEQUENCE LISTING

```
<160> NUMBER OF SEQ ID NOS: 9

<210> SEQ ID NO 1
<211> LENGTH: 525
<212> TYPE: PRT
<213> ORGANISM: Unknown
<220> FEATURE:
<223> OTHER INFORMATION: Synthetic construct of IDS protein

<400> SEQUENCE: 1

Ser Glu Thr Gln Ala Asn Ser Thr Thr Asp Ala Leu Asn Val Leu Leu
  1               5                  10                  15

Ile Ile Val Asp Asp Leu Arg Pro Ser Leu Gly Cys Tyr Gly Asp Lys
             20                  25                  30

Leu Val Arg Ser Pro Asn Ile Asp Gln Leu Ala Ser His Ser Leu Leu
         35                  40                  45

Phe Gln Asn Ala Phe Ala Gln Gln Ala Val Cys Ala Pro Ser Arg Val
     50                  55                  60

Ser Phe Leu Thr Gly Arg Arg Pro Asp Thr Thr Arg Leu Tyr Asp Phe
 65                  70                  75                  80

Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
```

-continued

```
            115                 120                 125
Ser Phe Pro Tyr His Pro Ser Ser Glu Lys Tyr Glu Asn Thr Lys
    130                 135                 140
Thr Cys Arg Gly Pro Asp Gly Glu Leu His Ala Asn Leu Leu Cys Pro
145                 150                 155                 160
Val Asp Val Leu Asp Val Pro Glu Gly Thr Leu Pro Asp Lys Gln Ser
                165                 170                 175
Thr Glu Gln Ala Ile Gln Leu Leu Glu Lys Met Lys Thr Ser Ala Ser
                180                 185                 190
Pro Phe Phe Leu Ala Val Gly Tyr His Lys Pro His Ile Pro Phe Arg
            195                 200                 205
Tyr Pro Lys Glu Phe Gln Lys Leu Tyr Pro Leu Glu Asn Ile Thr Leu
    210                 215                 220
Ala Pro Asp Pro Glu Val Pro Asp Gly Leu Pro Pro Val Ala Tyr Asn
225                 230                 235                 240
Pro Trp Met Asp Ile Arg Gln Arg Glu Asp Val Gln Ala Leu Asn Ile
                245                 250                 255
Ser Val Pro Tyr Gly Pro Ile Pro Val Asp Phe Gln Arg Lys Ile Arg
                260                 265                 270
Gln Ser Tyr Phe Ala Ser Val Ser Tyr Leu Asp Thr Gln Val Gly Arg
            275                 280                 285
Leu Leu Ser Ala Leu Asp Asp Leu Gln Leu Ala Asn Ser Thr Ile Ile
    290                 295                 300
Ala Phe Thr Ser Asp His Gly Trp Ala Leu Gly Glu His Gly Glu Trp
305                 310                 315                 320
Ala Lys Tyr Ser Asn Phe Asp Val Ala Thr His Val Pro Leu Ile Phe
                325                 330                 335
Tyr Val Pro Gly Arg Thr Ala Ser Leu Pro Glu Ala Gly Glu Lys Leu
                340                 345                 350
Phe Pro Tyr Leu Asp Pro Phe Asp Ser Ala Ser Gln Leu Met Glu Pro
            355                 360                 365
Gly Arg Gln Ser Met Asp Leu Val Glu Leu Val Ser Leu Phe Pro Thr
    370                 375                 380
Leu Ala Gly Leu Ala Gly Leu Gln Val Pro Pro Arg Cys Pro Val Pro
385                 390                 395                 400
Ser Phe His Val Glu Leu Cys Arg Glu Gly Lys Asn Leu Leu Lys His
                405                 410                 415
Phe Arg Phe Arg Asp Leu Glu Glu Asp Pro Tyr Leu Pro Gly Asn Pro
                420                 425                 430
Arg Glu Leu Ile Ala Tyr Ser Gln Tyr Pro Arg Pro Ser Asp Ile Pro
            435                 440                 445
Gln Trp Asn Ser Asp Lys Pro Ser Leu Lys Asp Ile Lys Ile Met Gly
    450                 455                 460
Tyr Ser Ile Arg Thr Ile Asp Tyr Arg Tyr Thr Val Trp Val Gly Phe
465                 470                 475                 480
Asn Pro Asp Glu Phe Leu Ala Asn Phe Ser Asp Ile His Ala Gly Glu
                485                 490                 495
Leu Tyr Phe Val Asp Ser Asp Pro Leu Gln Asp His Asn Met Tyr Asn
                500                 505                 510
Asp Ser Gln Gly Gly Asp Leu Phe Gln Leu Leu Met Pro
            515                 520                 525

<210> SEQ ID NO 2
```

```
<211> LENGTH: 48
<212> TYPE: DNA
<213> ORGANISM: Artificial Sequence
<220> FEATURE:
<223> OTHER INFORMATION: IDS 1 forward primer

<400> SEQUENCE: 2
ctatgggtat ctggtacctg tgggatgccg ccaccccgga ccggccga                    48

<210> SEQ ID NO 3
<211> LENGTH: 73
<212> TYPE: DNA
<213> ORGANISM: Artificial Sequence
<220> FEATURE:
<223> OTHER INFORMATION: IDS 2 forward primer

<400> SEQUENCE: 3
tgcagatatc cggagcaaga tggattcaca ggcccaggtt cttatgttac tgctgctatg       60
ggtatctggt acc                                                         73

<210> SEQ ID NO 4
<211> LENGTH: 28
<212> TYPE: DNA
<213> ORGANISM: Artificial Sequence
<220> FEATURE:
<223> OTHER INFORMATION: IDS 3 reverse primer

<400> SEQUENCE: 4
gggccctcaa ggcatcaaca actggaaa                                         28

<210> SEQ ID NO 5
<211> LENGTH: 48
<212> TYPE: DNA
<213> ORGANISM: Artificial Sequence
<220> FEATURE:
<223> OTHER INFORMATION: IDS N1 forward primer

<400> SEQUENCE: 5
cagcaagcag gtcattgttc caacatgccg ccaccccgga ccggccga                   48

<210> SEQ ID NO 6
<211> LENGTH: 49
<212> TYPE: DNA
<213> ORGANISM: Artificial Sequence
<220> FEATURE:
<223> OTHER INFORMATION: IDS N2 forward primer

<400> SEQUENCE: 6
tgcagatatc ccagctacag tcggaaacca tcagcaagca ggtcattgt                  49

<210> SEQ ID NO 7
<211> LENGTH: 24
<212> TYPE: DNA
<213> ORGANISM: Artificial Sequence
<220> FEATURE:
<223> OTHER INFORMATION: IDS 4 reverse primer

<400> SEQUENCE: 7
gaagatatcc cagggtgaaa gact                                             24

<210> SEQ ID NO 8
<211> LENGTH: 20
<212> TYPE: DNA
<213> ORGANISM: Artificial Sequence
<220> FEATURE:
<223> OTHER INFORMATION: T7 forward primer
```

<400> SEQUENCE: 8
aatacgactc actataggga                                                                            20

<210> SEQ ID NO 9
<211> LENGTH: 525
<212> TYPE: PRT
<213> ORGANISM: Unknown
<220> FEATURE:
<223> OTHER INFORMATION: Synthetic construct of IDS peptide variant
<220> FEATURE:
<221> NAME/KEY: MOD_RES
<222> LOCATION: (59)..(59)
<223> OTHER INFORMATION: Xaa = formylglycine

<400> SEQUENCE: 9

```
Ser Glu Thr Gln Ala Asn Ser Thr Thr Asp Ala Leu Asn Val Leu Leu
  1               5                  10                  15

Ile Ile Val Asp Asp Leu Arg Pro Ser Leu Gly Cys Tyr Gly Asp Lys
             20                  25                  30

Leu Val Arg Ser Pro Asn Ile Asp Gln Leu Ala Ser His Ser Leu Leu
         35                  40                  45

Phe Gln Asn Ala Phe Ala Gln Gln Ala Val Xaa Ala Pro Ser Arg Val
     50                  55                  60

Ser Phe Leu Thr Gly Arg Arg Pro Asp Thr Thr Arg Leu Tyr Asp Phe
 65                  70                  75                  80

Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320
```

```
Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
            515                 520                 525
```

COMPOSITION AND FORMULATION COMPRISING RECOMBINANT HUMAN IDURONATE-2-SULFATASE AND PREPARATION METHOD THEREOF

CROSS REFERENCE TO RELATED APPLICATIONS

This application is a National Stage of International Application No. PCT/KR2012/004734 filed Jun. 15, 2012, claiming priority based on Korean Patent Application No. 10-2012-0012718 filed Feb. 8, 2012 and U.S. Provisional Patent Application No. 61/500,994 filed Jun. 24, 2011, the contents of all of which are incorporated herein by reference in their entirety.

TECHNICAL FIELD

The present invention relates to a composition for the treatment of Hunter syndrome, comprising recombinant human iduronate-2-sulfatase (hereinafter referred to as "IDS"), a formulation comprising the same, and a method for preparing the same.

More particularly, the composition for the treatment of Hunter syndrome in accordance with the present invention comprises as an active ingredient IDS having an amino acid sequence represented by SEQ ID NO: 1, wherein cysteine residue at position 59 in the IDS amino acid sequence of SEQ ID NO: 1 is converted to formylglycine (FGly: 2-amino-3-oxopropionic acid) at a molar ratio of 65% or higher, preferably at a molar ratio of 75% or higher, and more preferably at a molar ratio of 80% or higher. The IDS peptide of SEQ ID NO: 1 wherein the amino acid residue at position 59 is formylglycine is identified as SEQ ID NO: 9. In addition, the IDS contained in the composition for the treatment of Hunter syndrome contains mannose-6-phosphate in an amount of 2.0 to 4.0 moles per mole of IDS, preferably in an amount of from 2.3 to 3.5 moles, and more preferably in an amount of from 2.5 to 3.0 moles.

The method for preparing the composition for the treatment of Hunter syndrome in accordance with the present invention comprises:

(1) culturing a recombinant cell strain transformed with a gene encoding IDS represented by SEQ ID NO: 1 and obtaining the culture; and (2) purifying the culture through anion exchange chromatography, hydrophobic chromatography, cation exchange chromatography, and affinity chromatography, characterized in that the recombinant cell strain is cultured in the presence of a hydrolysate and the cation exchange chromatography is performed using an eluting buffer with a pH of 4.0 to 6.0.

Having advantages over conventional products in terms of safety and pharmaceutical efficacy, the therapeutic composition comprising IDS and the formulation comprising the same can be effectively used to treat Hunter syndrome.

BACKGROUND ART

Hunter syndrome or mucosaccharidosis type II is a lysosomal storage disease (LSD) in which mucopolysaccharides, also known as glycosaminoglycans (GAG), are not broken down correctly and build up in the body due to a deficiency of IDS. As GAG continues to buildup throughout the cells of the body, various signs of Hunter syndrome become more visible. Physical manifestations for some people with Hunter syndrome include distinct facial features and a large head. Representative among the symptoms of Hunter syndrome are an enlarged abdomen due to hepatomegaly or splenomegaly, deafness, valvular heart disease, obstructive airway disease and sleep apnea. Also, major joints may be affected by Hunter syndrome, leading to joint stiffness and limited motion. In some cases of Hunter syndrome, central nervous system involvement leads to developmental delays and nervous system problems. Hunter syndrome is a known to occur at a rate of 1 in 162,000 and is a genetic disorder in the form of chromosome X-linked recessive and so given the great suffering to the family as well as the patient.

Various trials have been carried out thus regarding the treatment of Hunter syndrome, including bone marrow graft, enzyme replacement, and gene therapy. While bone marrow graft is able to stop most of the symptoms, it is difficult to find an HLA (human leukocyte antigen) match for all patients. Further, a bone marrow graft is a major surgical operation accompanied by several adverse effects, including the patient's life being put under high risk if the HLA is mismatched. Gene therapy for Hunter syndrome delivers a normal IDS gene into the body with the aid of a viral vector such as adenovirus or retrovirus or a non-viral vector. However, gene therapy remains an experimental technique, and has not been clinically applied. As for the enzyme replacement treatment for Hunter syndrome, it administers externally produced IDS and has the advantage of being simple. However, enzyme replacement must be continuously carried out, which incurs a high expense. Elaprase® (Shire Pharmaceuticals Group), produced using recombinant DNA technology, was approved by the FDA as an enzyme replacement treatment for Hunter syndrome. However, this drug is very expensive and suffers from the drawbacks of being poor in effect and safety.

As described above, although various therapies for Hunter syndrome have been developed, there is still a pressing need for a new therapy and agent that exhibits high therapeutic efficacy with high safety.

DISCLOSURE

Technical Problem

It is an object of the present invention to overcome the problems encountered in the prior art and to provide a composition for the therapy of Hunter syndrome, comprising recombinant IDS as an active ingredient, which guarantees high therapeutic efficacy and safety, as produced by improved culturing and purifying processes, and a formulation comprising the same.

It is another object of the present invention to provide a method for preparing the composition for the treatment of Hunter syndrome and the formulation comprising the same.

Technical Solution

To achieve the above object, the present invention provides a composition for the therapy of Hunter syndrome, comprising as an active ingredient a recombinant IDS having an amino acid sequence represented by SEQ ID NO: 1, wherein cysteine residue at position 59 is converted to formylglycine (FGly) at a molar ratio of 65% or higher, preferably at a molar ratio of 75% or higher, and more preferably at a molar ratio of 80% or higher.

IDS, herein also called iduronate-2-sulfatase or I2S, has a molecular size of 56 kDa when isolated and purified from the human liver, kidney or placenta (Bielicki, J. et al. (1990) *Biochem, J.*, 271: 75~86). IDS is expressed as a monomeric protein of 550 amino acids and is secreted into the medium as a mature active protein of 525 amino acids following cleavage of the 25 amino acid signal peptide. The molecular weight of IDS varies with glycosylation and was found to range from approximately 60 to 90 kDa upon treatment with endoglycosidase F, as measured by SDS-PAGE.

IDS contains two disulfide bonds and eight N-linked glycosylation sites and is produced as a glycoprotein after undergoing post-translation modification in which the N-linked glycosylation sites are occupied by complex, hybrid and high mannose type oligosaccharide chains in eukaryotes. Once secreted into the culture medium, IDS may be used as a drug after going through typical isolation and purification processes. IDS may be in the form of glycoproteins with various glycosylation patterns, depending on various factors, including, for example, IDS genetic recombination, transformation (e.g., used cell lines), culture and purification techniques.

In this invention, it is disclosed that the content of mannose-6-phosphate (M6P) and the conversion ratio of Cys-59 to FGly have a great influence on the therapeutic efficacy and safety of IDS. The presence of mannose-6-phosphate (M6P) residues allows specific binding of the enzyme to M6P receptors on the cell surface, leading to cellular internalization of the enzyme, targeting of lysosomes and subsequent catabolism of accumulated GAG. Biological activity of IDS is also dependent on a post-modification of the conserved cysteine (position 59) to formylglycine.

Unless stated otherwise, the term "IDS," as used herein, means a carbohydrate-attached IDS protein, that is, a glycosylated IDS. The IDS of the present invention preferably has an amino acid sequence of SEQ ID NO: 1, but is not limited thereto. It should be apparent to those who have ordinary knowledge in the art (hereinafter referred to as "ordinary artisan") that so long as it allows the IDS to retain the desired activity, any amino acid sequence in which mutations such as insertion, deletion and substitution occur on some amino acid residues of the amino acid sequence of SEQ ID NO: 1 falls within the scope of the present invention.

As used herein, the term "glycosylation pattern" of IDS refers to the profile of oligosaccharides bound to the eight glycosylation sites of the resulting IDS (e.g., glycosylation sites and kinds of oligosaccharides).

In one embodiment, the IDS contained in the composition for the therapy of Hunter syndrome in accordance with the present invention has the same amino acid sequence as is known (SEQ ID NO: 1), but has a different glycosylation pattern and a different conversion ratio of cysteine at position 59 to formyl glycine, as described above (refer to Examples 1-5 and 1-6).

That is, the IDS used in the composition for the therapy of Hunter syndrome according to the present invention has an amino acid sequence of SEQ ID NO: 1 with the conversion of cysteine at position 59 to formyl glycine (FGly) at a molar ratio of 65% or higher, preferably at a molar ratio of 75% or higher, and more preferably at a molar ratio of 80% or higher, whereas the conversion ratio in Elaprase is approximately 50% (Genet Med 2006:8(8):465-473). Formylglycine is known to be deeply involved in the ability of IDS to degrade the substrate, that is the activity of IDS. Thus, because the composition of the present invention and the conventional agent Elaprase are different, the composition and the formulation according to the present invention can exhibit higher therapeutic efficacy for Hunter syndrome than can the conventional agent Elaprase because of a greater cytosine to formylglycine conversion ratio at position 59 on the amino acid sequence of IDS.

In addition, the IDS used in the composition or the formulation for the therapy of Hunter syndrome in accordance with the present invention contains mannose-6-phosphate in an amount of from 2.0 to 4.0 moles per mole of IDS, preferably in an amount of from 2.3 to 3.5 moles and more preferably in an amount of from 2.5 to 3.0 moles. M6P plays an important role in the cellular internalization of IDS and subsequent targeting to intracellular lysosomes. Thus, the formulation of the present invention comprising IDS with a high content of M6P guarantees the high performance of the receptor-mediated uptake mechanism for this enzyme and targeting to lysosomes, thereby resulting in the effective catabolism of accumulated GAG.

The formulation for the therapy of Hunter syndrome comprising IDS in accordance with the present invention can be prepared by formulating the composition of the present invention with a pharmaceutically acceptable carrier into a suitable form.

As used herein, the term "pharmaceutically acceptable" carrier refers to a non-toxic, physiologically compatible vehicle for the active ingredient, which is suitable for ingestion by animals, without undue toxicity, incompatibility, instability, irritation, allergic response and the like.

The composition according to the present invention may be formulated with a suitable vehicle depending on the administration route taken. The formulation according to the present invention may be administered orally or parenterally but this is not limited to these. For parenteral administration, a route selected from among transdermal, intranasal, intraperitoneal, intramuscular, subcutaneous or intravenous routes may be taken.

For oral administration, the pharmaceutical composition may be formulated in combination with a suitable oral vehicle into powders, granules, tablets, pills, troches, capsules, liquids, gels, syrups, suspensions and wafers using a method known in the art. Examples of the suitable vehicle useful in the formulation include sugars such as lactose, dextrose, sucrose, sorbitol, mannitol, xylitol, erythritol and maltitol, starches such as corn starch, wheat starch, rice starch, and potato starches, celluloses such as cellulose, methyl cellulose, sodium carboxymethyl cellulose, and hydroxypropyl methyl cellulose, and fillers such as gelatin and polyvinylpyrrolidone. Optionally, the formulation may further comprise a disintegrant such as crosslinked polyvinylpyrrolidone, agar, alginic acid or sodium alginate. In addition, an anti-agglomerating agent, a lubricant, a wetting agent, a fragrant, an emulsifier, and a preservative may be further employed.

Also, the composition of the present invention may be formulated in combination with a parenteral vehicle into a parenteral dosage form such as an injectable preparation, a transdermal preparation or an intranasal inhalation using a method well known in the art. For use in injection, the formulation must be sterilized and protected from contamination with microorganisms such as bacteria and fungi. Examples of the vehicle suitable for injection may include, but are not limited to, water, ethanol, polyol (e.g., glycerol, propylene glycol, liquid polyethylene glycol, etc.), combinations thereof, and/or a vegetable oil-containing solvent or dispersion medium. More preferably, the vehicle may be an isotonic solution such as Hank's solution, a Ringer's solution, triethanol amine-containing PBS (phosphate buffered saline) or injectable sterile water, 10% ethanol, 40% propylene glycol and 5% dextrose. In order to protect the injectable preparation from microbial contamination, it may further comprise an antibacterial and antifungal agent such as paraben, chlorobutanol, phenol, sorbic acid, thimerosal, etc. Also, the injectable preparations may further comprise, in most cases, an isotonic agent such as sugar or sodium chloride. These formulations are disclosed in a document well known in the pharmaceutical field (Remington's Pharmaceutical Science, 15th Edition, 1975, Mack Publishing Company, Easton, Pa.). As concerns inhalation, the formulation according to the present invention may be delivered conveniently in the form of an aerosol spray from a compressed pack or sprayer using a suitable propellant, such as dichlorofluoromethane, trichlorofluoromethane, dichlorotetrafluoroethane, carbon dioxide or a suitable gas. In the case of compressed aerosol, the unit size of a dose may be determined by a valve for delivering a metered amount. For example, gelatin capsules and cartridges for use in an inhaler or insufflator can be formulated containing a powder mix of the compound and a suitable powder base such as lactose or starch for these systems.

Other suitable pharmaceutical vehicles are described in Remington's Pharmaceutical Sciences, 19th ed., Mack Publishing Company, Easton, Pa., 1995.

Moreover, the formulation according to the present invention may further comprise one or more buffers (e.g., saline or PBS), carbohydrates (e.g., glucose, mannose, sucrose or dextran), stabilizers (sodium hydrogen sulfite, sodium sulfite or ascorbic acid), anti-oxidants, bacteriostatics, chelating agents (e.g., EDTA or glutathione), adjuvants (e.g., aluminum hydroxide), suspending agents, thickeners and/or preservatives (benzalkonium chloride, methyl- or propyl-paraben and chlorobutanol).

Also, the composition of the present invention may be formulated into a dosage form that allows the rapid, sustained or delayed release of the active ingredient after being administered into mammals. An effective amount of the formulation thus prepared may be administered via a variety of routes including oral, transdermal, subcutaneous, intravenous and intramuscular routes. The term "effective amount," as used herein refers to an amount of IDS that allows tracing the diagnostic or therapeutic effect to take place when administered into a patient. The dose of the formulation according to the present invention may vary depending on various factors including, the route of administration, the type of subject to be treated, the type of disease to be treated, the administration route, the severity of the illness, and the patient's age, gender, weight, condition, and health state. The formulation comprising IDS according to the present invention may be used at a dose of from 0.1 to 10 mg/kg and preferably at a dose of from 0.5 to 1.0 mg/kg per dosage.

The method for preparing the therapeutic composition in accordance with the present invention comprises:

(1) culturing a recombinant cell strain transformed with a gene encoding IDS represented by SEQ ID NO: 1 and obtaining the culture; and (2) purifying the culture through anion exchange chromatography, hydrophobic chromatography, cation exchange chromatography, and affinity chromatography, wherein, the recombinant cell strain is cultured in the presence of a hydrolysate and the cation exchange chromatography is performed using an eluting buffer with a pH of 4.0 to 6.0.

More particularly, the method for preparing the therapeutic composition in accordance with the present invention comprises:

(1) transforming a host cell with an expression vector carrying a IDS gene to obtain a recombinant cell strain;

(2) culturing the recombinant cell strain in the presence of a hydrolysate in a serum-free medium and obtaining the culture;

(3) purifying IDS from the culture through anion exchange chromatography, hydrophobic chromatography, cation exchange chromatography and affinity chromatography, said cation exchange chromatography being performed using an eluting buffer ranging in a pH from 4.0 to 6.0; and (4) combining the purified IDS with a pharmaceutically acceptable carrier.

In the method, step (1) is directed to establishing a recombinant cell strain by introducing an expression vector carrying an IDS gene into a host cell. The amino acid sequence of IDS and a gene encoding IDS are known in the art. A gene that codes for the IDS having the amino acid sequence of SEQ ID NO: 1 is preferred, but is not provided as a limiting example. If an amino acid sequence retains the activity of IDS sought to be brought about by the purpose of the present invention, although mutated by insertion, deletion and/or substitution of some amino acid residues on the amino acid sequence of SEQ ID NO: 1, its gene may be used in the present invention. The expression vector carrying the gene may be constructed using a typical method known in the art. In addition, the expression vector may contain a marker gene which allows the introduction of the gene to be identified. Examples of the marker gene include a dihydrofolate reductase gene (dhfr), but are not limited thereto. Preferable is a pJK-dhfr-Or2-IDS vector (FIG. 2).

The host cells available for step (1) may be animal cells and their examples include, but are not limited to, Chinese hamster ovary (CHO) cells, human embryonic kidney (HEK) cells, baby hamster kidney (BHK) cells, monkey kidney cell 7 (COST), and NSO cells, with a preference for CHO cells. CHO cell lines are one of the most widely used in the production of biomedical products thanks to their high cell growth rates and productivity, ease of genetic manipulation, rapid proliferation in large-scale suspension cultures and high adaptation to protein-free media. The transformation in step (1) may be carried out according to a protocol known in the art.

In the method, step (2) is directed to culturing the recombinant cell strain anchoring the IDS expression vector therein in a serum-free medium. The culturing may be carried out in a medium and under conditions optimized for the kind of host cell. Preferred is a serum-free medium. Being free of sera (e.g., bovine sera), such media avoid the likelihood of inducing the side effects or risks associated with sera.

In one embodiment of the present invention, the culturing of the recombinant cell strain transformed with an IDS expression vector may be further scaled up. For example, the recombinant cell strain of the present invention may be cultured in a shaker flask and then scaled up to hundreds to thousands of liters in a bioreactor. The culturing step is carried out in the presence of a hydrolysate, which has an important influence on the determination of formylglycine content. Preferably, the hydrolysate is added in such an amount as to form a final concentration of 0.1~10.0 g/L. The hydrolysate useful in the present invention may be those obtained by hydrolyzing an animal or plant material. More particularly, the hydrolysate may be obtained by hydrolyzing at least one selected from the group consisting of, but not limited to, soybean, potato, wheat germ, and yeast.

In the method, step (3) is directed to the purification of IDS from the cell culture through anion exchange chromatography, hydrophobic chromatography, cation exchange chromatography, and affinity chromatography.

Preferably, the four chromatographic processes may be performed in that order. However, it should be obvious to an ordinary artisan that the order may be changed if necessary. Together with the order of the chromatographic processes, the resins and the pH values of the eluting buffers are important in determining the glycosylation pattern and formylglycine content of IDS.

Anion exchange chromatography is intended to remove dyes and various impurities from the cell culture and is performed on a column filled with Q Sepharose® resins using an eluting buffer with a pH of from 5.5 to 7.5.

Hydrophobic chromatography is intended to remove the dyes and impurities that remain after anion exchange chromatography. It is performed on a column filled with phenyl Sepharose® resins, using an eluting buffer at a pH of from 5.0 to 7.0.

Cation exchange chromatography is intended to select high the formylglycine content and remove remaining impurities. It is performed on a column filled with cation exchange resins, using an eluting buffer with a pH of from 4.0 to 6.0. Examples of the cation exchange resins useful in the present invention may include CM Sepharose Fast Flow, SP Sepharose Fast Flow, S Sepharose Fast Flow and Capto MMC, all from GE Healthcare, but are not limited thereto. Preferably, the eluting buffer ranges in pH from 4.0 to 6.0.

Affinity chromatography is intended to remove the glycerol used in the cation exchange chromatography and concentrate the volume of the eluates. It is performed on a column filled with Blue Sepharose™ resins, using an eluting buffer with a pH of from 6.0 to 8.0.

The conditions of each type of chromatography may be optimally modified by the ordinary artisan. With regard to concrete chromatography conditions, reference may be made to Example 1-5 described below.

The method for preparing the composition comprising IDS as an active ingredient in accordance with the present invention may further comprise inactivating viruses that may be incorporated into the composition. The inactivation may be conducted in various ways, and preferably by holding the culture at pH 3.0~4.0 or under a high pH condition for a predetermined time. The inactivating process may be achieved during the purification process, preferably during the chromatography, and more preferably between the hydrophobic chromatography and the cation exchange chromatography.

After the chromatographic processes, the active fraction thus obtained may be concentrated and filtered to afford IDS which can be used as the active ingredient of the pharmaceutical composition.

The composition may be mixed with a pharmaceutically acceptable carrier and formulated into a suitable dosage form.

The composition comprising the IDS, prepared by the method according to the present invention, has advantages over conventional IDS compositions as follows 1) it exerts higher pharmaceutical efficacy thanks to a higher formylglycine content, 2) it can more effectively catabolize GAG accumulated within lysosomes, 3) it is free of animal-derived serum and thus safe, and 4) it is safe and efficacious thanks to its purity of 99.9% or higher.

Advantageous Effects

The composition comprising the recombinant IDS and the formulation comprising the same in accordance with the present invention are superior in pharmaceutical efficacy and safety to the conventional agent Elaprase and thus can be effectively used for the therapy of Hunter syndrome.

DESCRIPTION OF DRAWINGS

FIG. 6 is a view showing the amino acid sequence of the IDS of the present invention as analyzed by MALDI-MS/MS and LC-ESI-MS/MS.

FIG. 10 is a view indicating the positions of disulfide bonds in the IDS of the present invention, obtained through MALDI-MS/MS.

MODE FOR INVENTION

A better understanding of the present invention may be obtained through the following examples which are set forth to illustrate, but are not to be construed as limiting the present invention.

Example 1

Preparation of IDS

<1-1> Gene Acquisition

Peripheral blood mononuclear cells (PBMC) were isolated from human blood as described previously [S. Beckebaum et al., *Immunology*, 2003, 109:487-495]. Total RNA was extracted from the PBMC according to a protocol described previously [M. J. Holland et al., *Clin. Exp. Immunol.*, 1996, 105:429-435]. In order to construct a cDNA library from the total RNA, single-stranded cDNA was synthesized using oligo-(dT) primer with the aid of a single-strand synthesis kit (Boehringer mannheim). In this regard, DEPC-treated distilled water was added to an eppendorf tube containing 1 µg of the total RNA so as to form a final volume of 12.5 µL. Then, 1 µL of a 20 pmol oligo(dT) primer was added to the tube, followed by incubation at 70° C. for 2 min and cooling. To this reaction mixture were added 4 µL of a reaction buffer, 1 µL of dNTP, 1 µL of an RNase inhibitor, and 1 µL of reverse transcriptase which were then reacted at 42° C. for one hour to synthesize single stranded cDNA. PCR was performed on the cDNA as a template in the presence of primers of SEQ ID NOS: 2 to 4 to amplify a human IDS gene. In this context, each primer was designed to contain a restriction enzyme recognition site for use in gene cloning.

<1-2> Construction of Expression Vector

A. Construction of pJK-dhfr-IDS-S1 Vector

Figure 1:
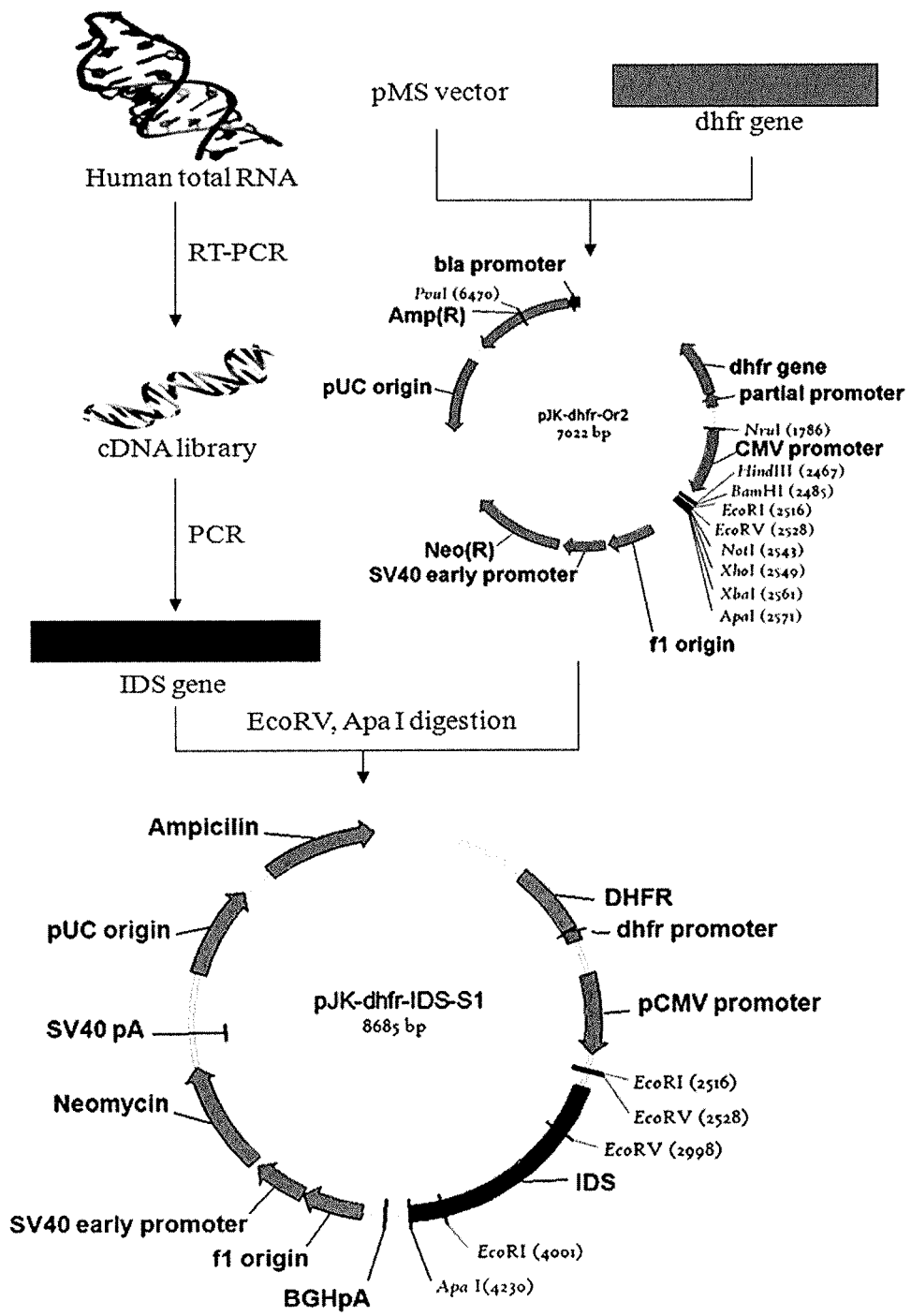
FIG. 1 is a view illustrating a scheme for constructing the pJK-dhfr-IDS-S1 vector used to construct an IDS expression vector.

A light chain signal sequence of an antibody (derived from a part of the human IgG light chain) as a non-coding sequence was introduced into the 5'-terminus of the IDS gene acquired by Example <1-1> before PCR. After the PCR product obtained thereby was run on gel by electrophoresis, the human IDS gene was isolated using a gel extraction kit. The isolated IDS gene and the pJK-dhfr-Or2 vector (Aprogen) were digested with EcoRV and ApaI and ligated to each other at 16° C. for 20 hours. The recombinant vector thus constructed was transformed into *E. coli* (DH5α) which was then spread over an LB plate containing 50 µg/mL ampicillin and incubated overnight. Colonies grown on the plates were selected and cultured so as to isolate the plasmid therefrom (FIG. 1).

B. Construction of Recombinant Human IDS Expression Plasmid

In order to change the non-coding sequence of the plasmid constructed above to a signal sequence, the recombinant human IDS was subcloned to a pJK-dhfr-Or2 vector. To this end, the pJK-dhfr-IDS-S1 vector was digested with EcoRV and ApaI to give a partial IDS gene (1233 bp) which was then inserted into the pJK-dhfr-Or2 vector previously treated with the same restriction enzymes, to construct a pJK-dhfr-IDS-S2 vector. In order to introduce a non-coding sequence and a signal sequence to the 5'-terminus, an IDS N1 forward primer (SEQ ID NO: 5) and an IDS 4 reverse primer (SEQ ID NO: 7) were used for PCR with the pJK-dhfr-IDS-S1 vector serving as a template. After starting at 94° C. for 5 min, PCR was performed with 30 cycles of 94° C. for 1 min, 55° C. for 30 sec and 72° C. for 40 sec and finished by extension at 72° C. for 10 min.

The PCR amplification afforded a partial IDS gene that was 448 bp. This gene was used as a template for the PCR which was performed again in the presence of an IDS N2 forward primer (SEQ ID NO: 6) and an IDS 4 reverse primer (SEQ ID NO: 7) under the same conditions as described above. This resulted in the synthesis of a DNA fragment 476 bp long.

Figure 2:
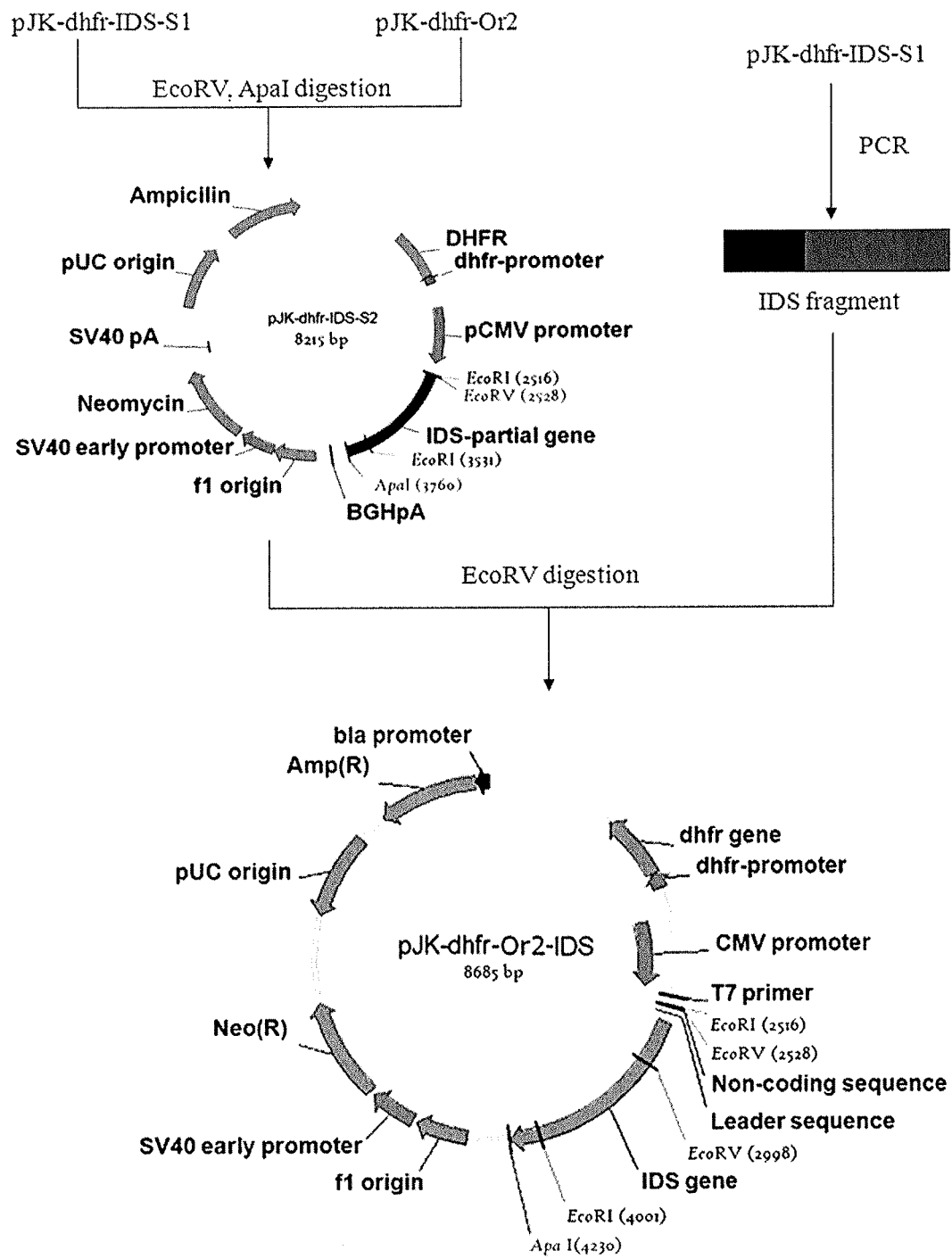
FIG. 2 is a view illustrating a scheme for constructing the IDS expression vector pJK-dhfr-Or2-IDS from the pJK-dhfr-IDS-S1 of FIG. 1.

Subsequently, the pJK-dhfr-IDS-S2 vector and the recombinant human IDS gene fragment (476 bp) were separately digested with EcoRV. The digests were separated on gel by electrophoresis to obtain the vector and the 476 bp-long IDS fragment. These vector and insert were ligated at 16° C. for 12 hours in the presence of T4 DNA ligase to construct pJK-dhfr-Or2-IDS plasmid. These procedures are illustrated in FIG. 2.

To confirm the construction of the IDS expression plasmid, DH5α was transformed with pJK-dhfr-Or2-IDS and cultured for 24 hours on an LB plate containing ampicillin (50 µg/mL). From the colonies thus formed, a plasmid was isolated and digested to measure the size of the insert. Also, base sequencing was conducted using a T7 primer (SEQ ID NO: 8).

<1-3> Selection of Recombinant Human IDS Expression Strain

A. Transfection of CHO-DG44

CHO-DG44 was used as a host cell for expressing the IDS of the present invention. The mutant Chinese hamster ovary cell CHO-DG44 carries a double deletion for the endogenous dhfr (dihydrofolate reductase) gene which encodes DHFR enzyme. The DHFR enzyme is involved in the conversion of folate through dihydrofolate (FH2) into tetrahydrofolate (FH4) which is involved in the de novo synthesis of nucleic acids. The level of dhfr in the cells is dependent on the concentration of MTX. MTX, which is structurally similar to folic acid, a substrate of DHFR, competes with folic acid for binding dihydrofolate reductase, so that most dihydrofolate reductase loses its activity in the presence of MTX. Hence, if cells do not amplify a sufficient amount of dhfr, they die because they cannot synthesize nucleic acids necessary for their life. In contrast, if the amplification is sufficient, the cells can survive under a high concentration of MTX because they are relatively abundant in dhfr. This system may be applied to animal cells to select a transfected cell line which can amplify the dhfr gene and thus a structural gene of interest.

To this end, a dhfr gene was introduced as an amplifiable marker into the IDS expression vector pJK-dhfr-Or2-IDS, constructed in Example 1-2, and gene amplification was conducted using MTX and the dhfr gene.

In this regard, the DG44 cell line (obtained from Dr. Chaisin, Columbia University) was suspended in 10 mL of DMEM/F12 (supplemented with nucleotides and nucleosides, and 10% fetal bovine serum (FBS)) and harvested by spinning at 1000 rpm for 5 min. The cells were inoculated into 50 mL of a culture medium in a T-175 flask and incubated at $37\pm1°$ C. in a $5\pm1\%$ $CO_2$ incubator. One day before transfection, the culture medium for DG44 cells was removed from the T-175 flask and the cells were washed twice with PBS and detached by trypsinization. Then, they were seeded at a density of $5\times10^5$ cells into a T-25 flask and cultured at $37\pm1°$ C. for 24 hours in a $5\pm1\%$ $CO_2$ incubator. Bacterial or fungal contamination was examined under an optical microscope while PCR-ELISA was performed to examine whether the cells were contaminated with mycoplasma.

The germ-free DG-44 cells were transfected with the IDS expression vector pJK-dhfr-Or2-IDS, constructed in Example 1-2, using a Lipofectamine kit. In this regard, 5 µg of the expression vector and 50 µL of Lipofectamine were separately diluted in 800 µL of Opti-MEM I, mixed carefully so as not to form bubbles, and left at room temperature for 15 min. Meanwhile, DG44 cells were washed once with sterile PBS and three times with Opti-MEM I. To the DG44 cells were carefully added the DNA-lipofectamine mixture and then 6.4 mL of Opti-MEM before incubation at $37\pm1°$ C. for 5 hours in a $5\pm1\%$ $CO_2$ incubator. Thereafter, the incubation was conducted for an additional 48 hours in the medium supplemented with 8 mL of DMEM/F12 and 1.6 mL of FBS to promote the recovery of cell membranes and the growth of cells.

B. Selection of Geneticin (G418)-Resistant Cell Strain

The cultured cells were detached with 0.25% trypsin, counted, and seeded at a density of $5\times10^3$ cells/well into 96-well plates containing 100 µL of MEM-alpha medium (supplemented with 10% dialyzed FBS and 550 µg/mL G418) per well. Next day, the same medium was added in an amount of 100 µL/well and the cells were cultured for 2-3 weeks to form colonies. When the cells grew to 50% confluency, the medium was replaced with a fresh one. After maintenance for days, the culture media were collected for enzyme analysis.

The medium was replaced with 200 µL of a fresh medium every three days. On day 3~4 after culturing, non-transfected cells, that is, cells that were not resistant to geneticin started to detach from the bottom of the 96-well plates when observed with an optical microscope. The selected clones were cultured while being sequentially transferred from the 96-well plates to 24-well plates, 6-well plates and 100-mm dishes in the order. When the cells grew to 80~90% confluency in 100-mm dishes, the expression level was measured again. The cells were detached with 0.25% trypsin, counted and plated at a density of $5\times10^5$ cells/well/3 mL into 6-well plates, maintained for 3 days and counted. The expression level of the protein was quantitatively analyzed. According to the analysis results, 15 clones were selected.

C. Selection of IDS Expression Strain with High Expression Capacity

The 15 selected clones were cultured at an increased concentration of MTX to select cell strains in which IDS was amplified.

In this context, the cells were inoculated at a density of $1\times10^6$ cells/100 mm dish/10 mL of a medium containing MTX and cultured to 80~90% confluency. One tenth of the volume of the cell culture was inoculated again into 100 mm dish/10 mL. This sub-culturing process was repeated twice. The cells were allowed to undergo at least three passages so that they were sufficiently adapted to increased MTX concentrations. The concentration of MTX was increased, from 5 nM for the clones selected after conducting an analysis for the first three days, to 20 nM. In each step, the clones adapted to the increased MTX concentration were cultured for three days to measure cell growth rates. IDS expression levels were measured to select cell strains in which the amplification of the IDS gene took place, that is, cell strains in which the recombinant IDS was expressed at a high rate. Of the selected cell strains, NI4 was used in subsequent experiments because it had the highest expression level.

D. Selection of Single Strain by Limiting Dilution

There was the possibility that the strain NI4 might have become mixed with other strains. Hence, the strain was separated into a single strain. The N14 clones which survived 20 nM MTX were subcloned through limiting dilution so as to select a desired cell strain.

First, NI4 was inoculated at a density of 0.5 cells/well into IMDM medium (Gibco BRL, Cat#12200) in 96-well plates and cultured with the medium replenished every three days. On day three, the plates were observed under a microscope to exclude the wells in which two or more colonies had been formed per well. The wells in which only one colony had formed per well were selected and continued to be cultured. After culturing for 15 days, the cells were sub-cultured to 96-well plates and when cells had grown to 90% confluency, the medium was freshly replenished.

A total of 263 single strains were identified from the N14 strain. Of them, strain S46 was found to have the highest IDS activity and named NI4-S46.

<1-4> Cell Culture

A. Shaker Flask Culture

The NI4-S46 strain was cultured on a large scale to produce the IDS of the present invention. The strain was inoculated into an EX-cell 302 serum-free medium (containing glutamine, dextran sulfate, and pluronic F-68) in 125 mL culture flasks and cultured at $37\pm1°$ C. in a $5\pm1\%$ $CO_2$ incubator. Subsequently, the cells were passaged at a ratio of 1:5~1:8 every two to three days using shaker flasks. Upon the passage, the culture volume was gradually increased to approximately 2,400 mL. In many shaker flasks, the cells were cultured to a level sufficient to be inoculated into a fermentor.

B. Culture in 30 L Fermentor (Working Volume 20 L)

When the density of the cells in the shaker flasks reached $1.3\times10^6$ cells/mL, they were inoculated into a 30 L fermentor. During cell culturing, the culture conditions were kept at a dissolved oxygen content of 10% or higher, a culture temperature of $37\pm1°$ C. and a pH of $7.0\pm0.2$. If necessary, cell samples were taken and observed under a microscope. The cell culture was examined to analyze cell count, cell viability, pH, glucose concentration and glutamine concentration. On the basis of the analysis results, when it was decided that the cells were sufficiently grown, the cells were inoculated into a 150 L fermentor.

C. Culture in 150 L Fermentor (Working Volume 100 L)

When the cells in a 30 L fermentor reached a density of $0.9\times10^6$ cells/mL or higher, they were inoculated into a 150 L fermentor. During cell culturing, the culture condition was kept at a dissolved oxygen content of 10% or higher, a culture temperature of $37\pm1°$ C. and a pH of $7.0\pm0.2$. If necessary, cell samples were taken and observed under a microscope. The cell culture was examined to analyze cell count, cell viability, pH, glucose concentration and glutamine concentration. On the basis of the analysis results, when it was decided that the cells were sufficiently grown, the cells were inoculated into a 650 L fermentor.

D. Culture in 650 L Fermentor (Working Volume 500 L)

When the cells in a 150 L fermentor reached a density of $0.9\times10^6$ cells/mL or higher, they were inoculated into a 650 L fermentor. During cell culturing, the culture condition was kept at a dissolved oxygen content of 10% or higher, a culture temperature of $34\pm1°$ C. and a pH of $6.9\pm0.2$ for three days and then, at a culture temperature of $32\pm1°$ C. and a pH of $6.9\pm0.2$. If necessary, cell samples were taken and observed under a microscope to analyze cell counts, cell viability, pH, glucose concentrations and glutamine concentrations. Depending on the analysis result, glucose and glutamine concentrations were adjusted to continue cell growth. During the fermentation, a hydrolysate was added to increase the formylglycine conversion.

<1-5> Purification of IDS

IDS was isolated from the cell culture using a series of the following four chromatographic processes.

A. Harvest and Filtration of Culture Medium

When the cell viability remained in the range of 80~85% 10 days after inoculation into the 650 L fermentor, culturing was stopped. The cells were harvested from the culture using the Millipore POD filter system and D0HC filter (Millipore) at a pressure of 0.9 bar or less. After the cells were removed, the supernatant was filtered through a pre-filter (Millipore, 0.5+0.2 µm) and a 0.45+0.2 µm filter and recovered in a disposable sterile vinyl bag. The harvested culture solution was stored at 2~8° C.

B. Concentration and Diafiltration

The filtrate recovered in A was about 10-fold concentrated using an ultrafiltration system (Tangential Flow Filtration Membrane System). The membrane (cutoff: 30K, Pall) installed inside the ultrafiltration system was washed with WFI (water for injection) at a flow rate of 20~25 L/min and then equilibrated with a buffer (pH 7.0~8.0) containing 20 mM sodium phosphate (sodium dihydrogen phosphate monohydrate and sodium hydrogen phosphate heptahydrate). After equilibration, the filtrate was fed into the membrane while recovering the fractions that did not pass the membrane. Once the recovered volume became about 1/10 of the initial volume of the filtrate, the concentration procedure was stopped. The buffer was consecutively exchanged in a volume three to four times as large as that of the concentrate. If the conductivity and the pH fell within the criteria, the process was stopped. [criteria—conductivity: ≤5.0 mS/cm, pH 7.0~8.0].

C. Anion Exchange Chromatography

To remove dyes and various impurities from the concentrate recovered in B, anion exchange chromatography was conducted on a column (GE Healthcare) filled with Q Sepharose resins (GE Healthcare). The column was equilibrated with equilibrium buffer (pH 7.0~8.0) containing 20 mM sodium phosphate (sodium dihydrogen phosphate monohydrate and sodium hydrogen phosphate heptahydrate). The concentrate obtained in B was filtered through a 0.45+0.2 μm filter (Sartorius) and loaded at a flow velocity of 100~120 cm/h into the equilibrated column. After the loading was completed, the column was primarily washed with the equilibrium buffer and then with washing buffer (pH 5.5~7.5) containing sodium chloride. Subsequently, a target protein was eluted with an eluting buffer (pH 5.5~7.5) containing sodium chloride.

D. Hydrophobic Chromatography

To remove the dyes and impurities that remained after anion exchange chromatography, hydrophobic chromatography was performed on a column (GE Healthcare) filled with phenyl Sepharose resins (GE Healthcare). The column was equilibrated with equilibrium buffer (pH 5.0~7.0) containing sodium chloride. The eluate obtained in C was filtered through a 0.45+0.2 μm filter (Sartorius) and loaded at a flow velocity of 70~100 cm/h into the equilibrated column. After the loading was completed, the column was washed with the equilibrium buffer. Subsequently, a target protein was eluted with an eluting buffer (pH 5.0~7.0) containing glycerol.

E. Inactivation of Virus by Low pH

Viruses that may be derived from host cells or any material used in the processes carried out were inactivated by a low pH condition. In this regard, the eluate obtained in D was maintained for 2 hours at a pH 3.0~4.0 to which its acidity was adjusted with 25% acetic acid. Thereafter, the pH of the eluate was increased to 4.0~5.0 using 0.5 M sodium hydroxide for use in the next process. The inactivation by low pH was conducted at 12±2° C.

F. Cation Exchange Chromatography

IDS is glycoprotein with oligosaccharides, and exists as an isomer that has a different isoelectric point according to the content of sialic acid at the end of the Glycan chain. As oligosaccharides with a negative charge, sialic acid shows a difference in terms of the degree of binding to cation exchange resin according to the content of sialic acid. Using this characterization, cation exchange chromatography was conducted to obtain IDS showing high activity (a high content of formylglycine) with a high content of sialic acid and to remove other impurities [Product impurity (Aggregated IDS, processed IDS), process impurity (Host Cell protein)]. In detail, a column filled with cation exchange Capto™ MMC resins (GE Healthcare) was equilibrated with glycerol-added equilibration buffer (pH 4.0~5.0). The inactivated eluate obtained in E was filtered through a 0.45+0.2 μm filter (Sartorius) and loaded at a flow velocity of 100~120 cm/h onto the equilibrated column. Subsequently, the column was washed with the equilibration buffer, followed by elution with glycerol-added eluting buffer (pH 4.0~6.0) to give IDS with a high sialic acid content (isoelectric point 3.5 or less), high activity (formylglycine content: 80±15%) and high purity (SE-HPLC, 98% or higher).

G. Affinity Chromatography

Affinity chromatography (Blue Sepharose, GE Healthcare) was conducted to remove the glycerol used in the cation exchange chromatography and to reduce the volume of the eluate. The eluate obtained in F was filtered through a 0.45+0.2 μm filter (Sartorius) and loaded at a flow velocity of 100~120 cm/h onto a Blue Sepharose resin-filled column (GE Healthcare) that was previously equilibrated with glycerol-added equilibration buffer (pH 4.5~5.5). After completion of the loading, the column was washed with washing buffer (pH 4.5~5.5) and the target protein was eluted with eluting buffer (pH 6.0~8.0).

H. Concentration and Buffer Exchange

An ultrafiltration system (Tangential Flow Filtration Membrane System) was used to adjust the protein concentration of the eluate obtained in G and to exchange the buffer of the purified protein with formulation buffer. The membrane (cut-off: 10K, Pall) installed inside the ultrafiltration system was washed with WFI (water for injection) at a flow rate of 450~650 mL/min and then equilibrated with a formulation buffer (2.25 g/L sodium dihydrogen phosphate monohydrate, 0.99 g/L sodium hydrogen phosphate heptahydrate, 8 g/L sodium chloride, pH 6.0~7.0) without polysorbate 20, followed by concentrating the target protein. The buffer was consecutively exchanged in a volume three to four times as large as that of the concentrate. If the conductivity and the pH fell within the criteria, the process was stopped. [criteria—conductivity: 15.0±3.0 mS/cm, pH 6.0~7.0]. Adjust the content of the concentrated solution to 4.0±0.5 mg/mL.

I. Nanofiltration

Using a nano filter (NFP, Millipore), nano filtration was performed to remove viruses that might have come from the host cells or any of the materials used. Integrity test for filter is performed after washing the nano filter with water for injection. Once the integrity test was passed, the nanofilter was equilibrated with 1 L of formulation buffer (2.25 g/L sodium dihydrogen phosphate monohydrate, 0.99 g/L sodium hydrogen phosphate, 8 g/L sodium chloride, pH 6.0~7.0) without polysorbate 20. After completion of equilibration, the concentrate obtained in H was passed through the filter at a pressure of about 2 bar to produce a nano-filtrate. After filtration was completed, the filter was washed with the formulation buffer (post wash solution). After combining the nano filtration solution and the post wash solution, protein content is measured.

J. Drug Substance

The protein concentration of the filtrate obtained in I was adjusted with formulation buffer without polysorbate 20. After the addition of polysorbate, the solution was filtered through a 0.2 μm filter to produce a drug substance. The drug substance was aliquoted and stored in a deep freezer (−70±10° C.) until use.

K. Drug Product (Filling, Labeling, Packaging)

The stock stored in a deep freezer was thawed in a water bath maintained at 28±1° C. and diluted to a protein concentration of about 2.05±0.2 mg/mL using formulation buffer (2.25 g/L sodium dihydrogen phosphate monohydrate, 0.99 g/L sodium hydrogen phosphate heptahydrate, 8 g/L sodium chloride, 0.23 g/L polysorbate 20, pH 6.0~7.0). Thereafter, the dilution solution was filtered through a 0.2 μm filter to produce a final bulk solution. This final bulk solution was filled in 6 mL vial with approximately 3.3 g using auto filling. Once an vial inspection test was passed, the vials were packed to produce a drug product.

Figure 3:
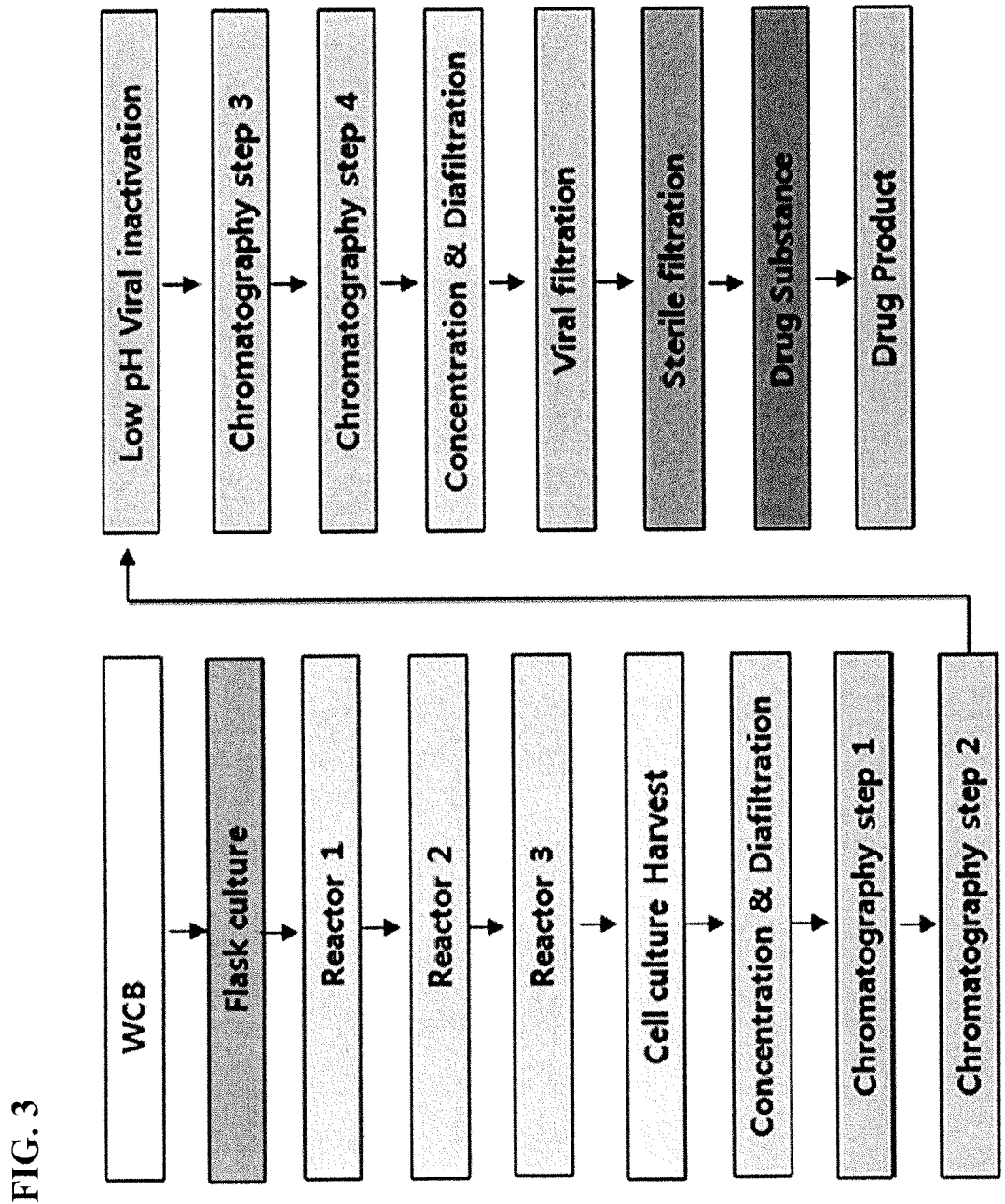
FIG. 3 is a flow chart illustrating the isolation and purification of IDS from transformed CHO-DG44.
Figure 4:
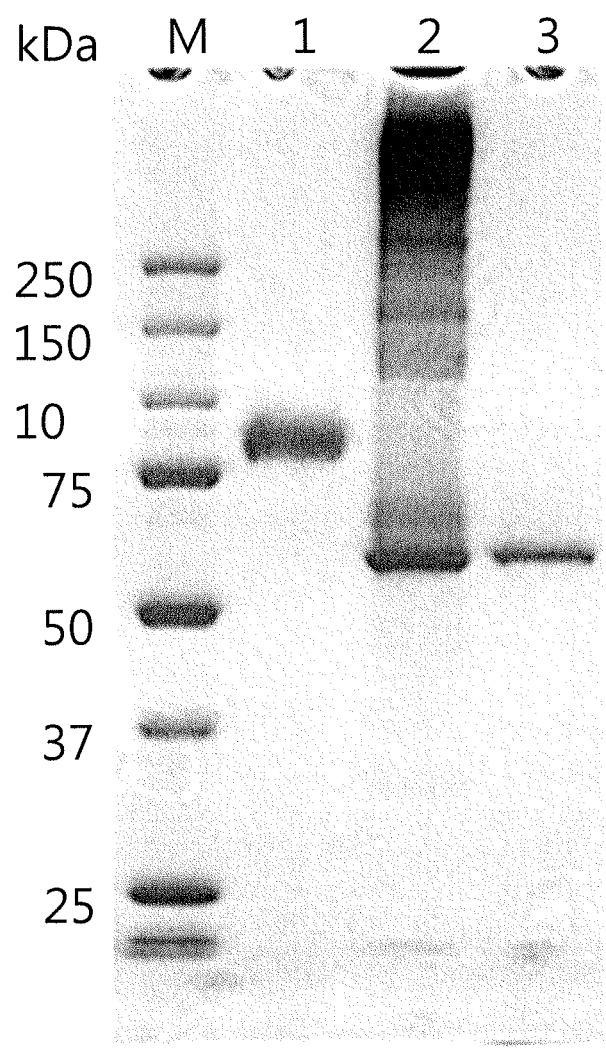
FIG. 4 is a photograph showing an SDS-PAGE result of IDS for analyzing the N-terminal sequence where a marker was run on lane M, glycosylated IDS on lane 1, PNGase F on lane 2, and deglycosylated IDS on lane 3.

The procedure from strain culturing to final product production is illustrated in FIG. 3.

Comparative Example 1

Preparation of Elaprase®

Elaprase®, commercially available recombinant IDS, was used as a comparative example.

Experimental Example 1

Structural Analysis and Characterization of Inventive IDS

<1-1> Amino Acid Sequencing—Internal Sequencing

Figure 5:
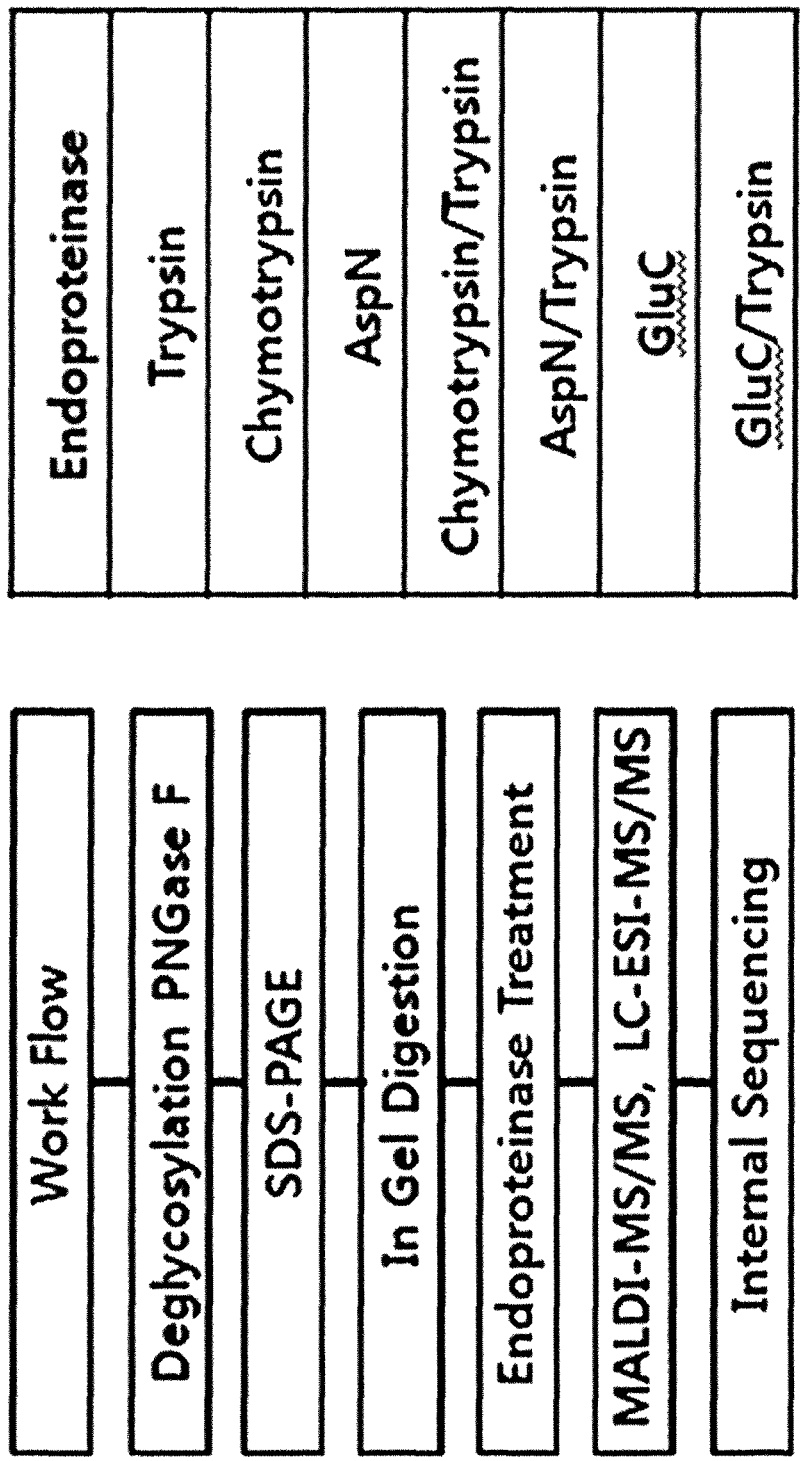
FIG. 5 is a flow chart illustrating the process of analyzing the amino acid sequence of IDS.

Deglycosylated IDS was separated by SDS-PAGE, followed by gel slicing. Then, digests resulting from treatment with various endoprotenases (trypsin, chymotrypsin, AspN, chymotrypsin/trypsin, AspN/trypsin, GluC and GluC/trypsin) were analyzed using MALDI-MS/MS and LC-ESI-MS/MS (FIG. 5). As a result, a total of 525 amino acid sequences were identified. The amino acid sequences coincided with the theoretical sequence of human IDS (FIG. 6).

<1-2> Disulfide Bond Analysis

Figure 7:
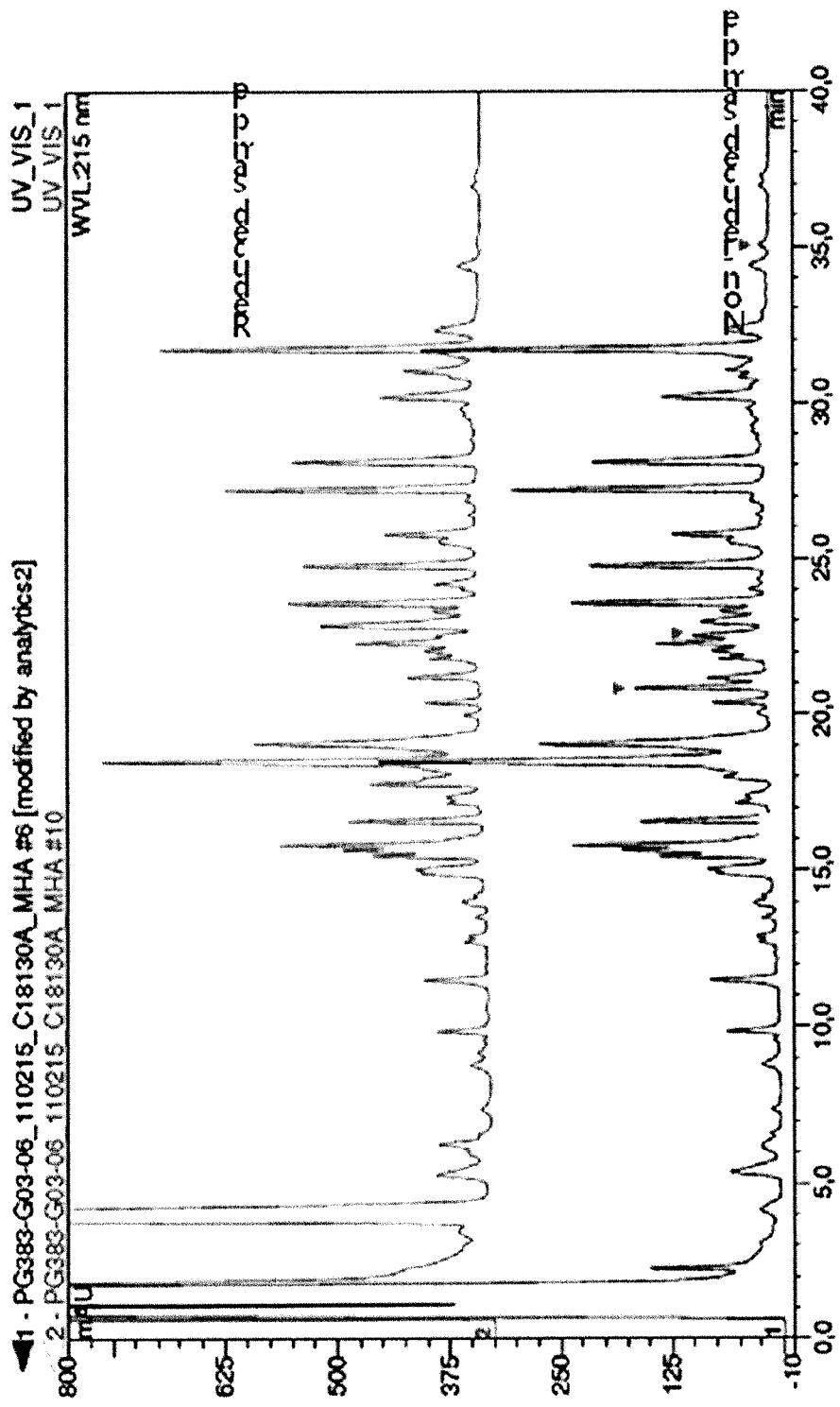
FIG. 7 is an RP-HPLC chromatogram of non-reduced and reduced IDS samples showing the position of disulfide bonds in IDS.

In a polypeptide, a disulfide bond is a covalent linkage, usually derived by the coupling of two SH groups of cysteine residues, playing an important role in stabilizing the higher structure of proteins. Theoretically, the 525 amino acids of IDS contain six cysteine residues, four of which form disulfide bonds. In this example, the location of cysteine residues responsible for the disulfide bonds of IDS was identified. First, IDS was deglycosylated by treatment with PNGase F to exclude the interference of sugars. In order to prevent the cysteine residues that do not take part in the formation of disulfide bonds from acting as an interfering factor, 4-vinylpyridine was used to convert IDS into a non-reduced sample so that the SH groups are restrained from randomly forming S—S bonds. Meanwhile, the disulfide bonds were cleaved by DTT, followed by blocking with 4-vinylpyridine to give a reduced sample. Trypsin and AspN, selected on the result of Experimental Example 1-3, were applied to the non-reduced and the reduced sample. The peptide fragments thus obtained were separated by RP-HPLC. RP-HPLC chromatograms of the non-reduced and the reduced samples were compared so as to discriminate the peaks that were found in the non-reduced sample, but not in the reduced sample (FIG. 7).

Figure 8:
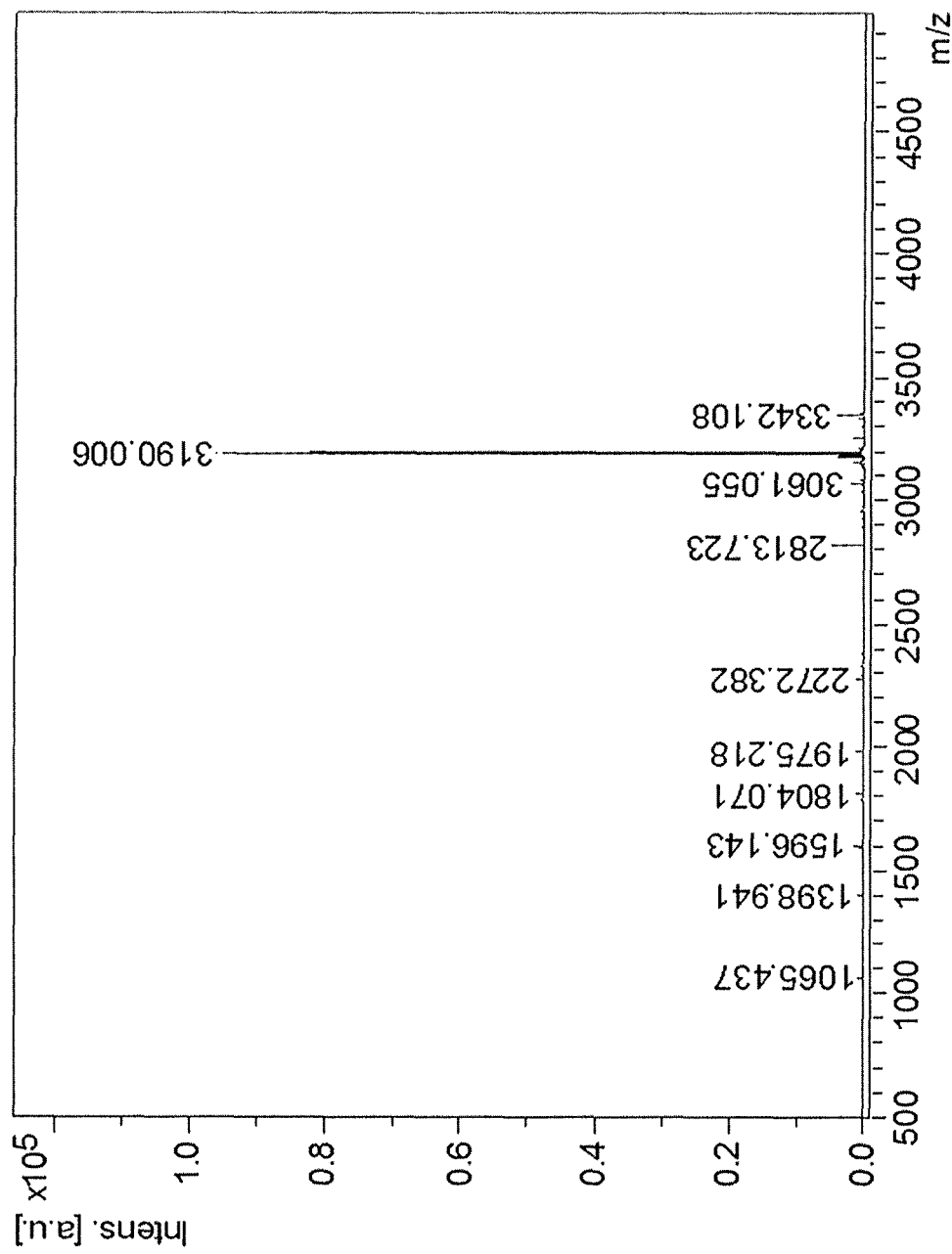
FIG. 8 is a view showing the positions of disulfide bonds in the IDS of the present invention as analyzed by MALDI-MS.

For more exact analysis, fractions at the discriminated peaks were reduced in size by additional treatment with endoproteinases, and the peaks containing disulfide bonds were analyzed using MALDI-MS (FIG. 8).

Figure 9:
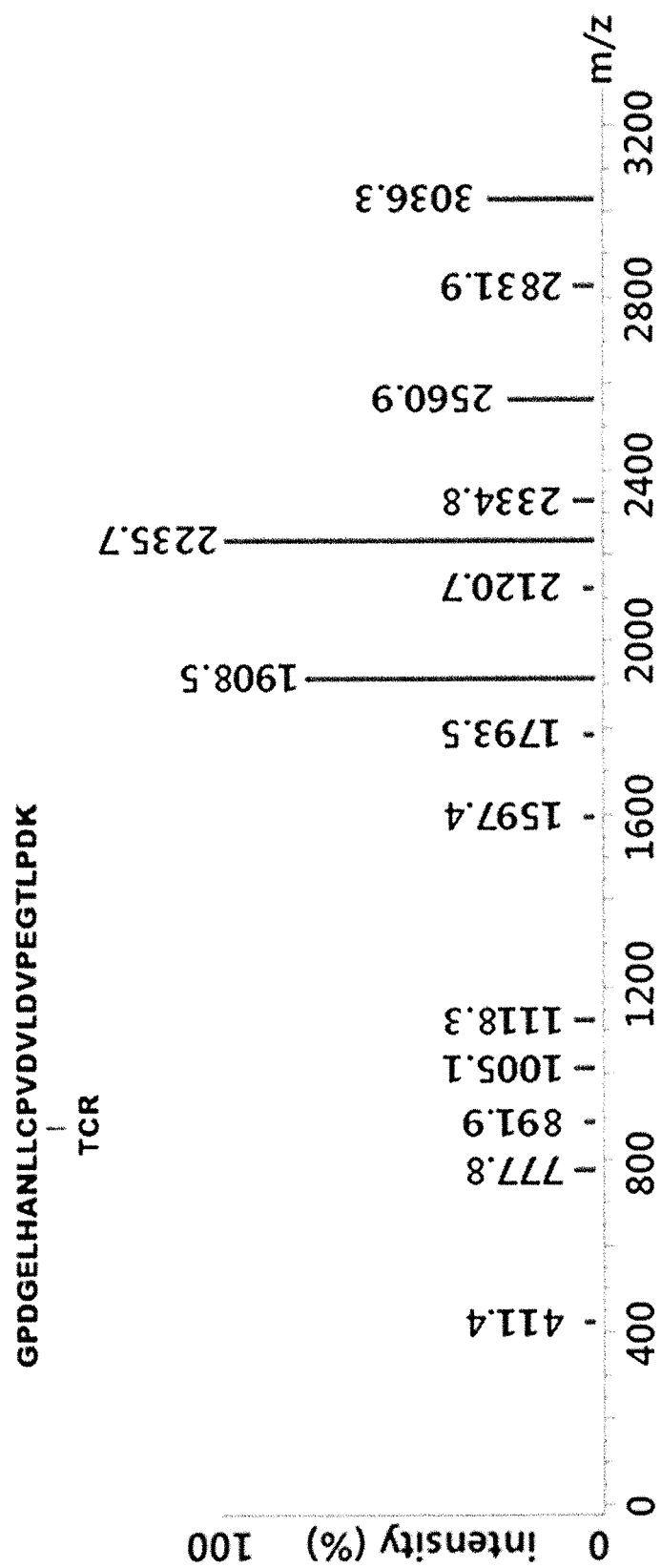
FIG. 9 is a view showing the positions of disulfide bonds in the IDS of the present invention as analyzed by MALDI-MS/MS.

Peaks with disulfide bonds were again sequence analyzed using MALDI-MS/MS (FIG. 9) to examine the positions of cysteine residues that form disulfide bonds among the 525 IDS amino acid residues. As shown in FIG. 10, disulfide bonds were observed to form between C146-C159 and between C397-C407.

<1-3> Analysis of Formylglycine Content

IDS degrades heparan sulfate and dermatan sulfate, both of which are a kind of glycosaminoglycan (GAG). This degradation activity is not acquired until the cysteine residue at position 59 in the active site (Cys59) is converted into formylglycine (FGly) by post-translational modification. Thus, the degradation activity of IDS was analyzed by examining the post-translational modification of Cys59 to FGly. For this analysis, AQUA (absolute quantification), a quantitative analysis method based on MS (Mass Spectroscopy), was used, in which a radio-labeled synthetic substrate (AQUA peptide) was spiked into a sample. To quantitatively analyze formylglycine at Cys59 position, a serial dilution of AQUA peptide was spiked into a sample and a calibration curve was drawn. Ratios of FGly-type peptide to Cys-type peptide were measured by LC-ESI-MS analysis, and applied to the AQUA calibration curve to calculate the content of formylglycine.

This analysis determined the conversion of Cys59 to FGly at a rate of 80±15%. In consideration of the Cys50 to FGly conversion rate of about 50% in the commercially available agent Elaprase (Elaprase Science Discussion, EMEA, 2007; Genet Med 2006:8(8):465-473), the therapeutic composition comprising the IDS of the present invention and the formulation prepared with the composition is anticipated to have much higher therapeutic activity compared to Elaprase.

<1-4> Identification of Glycosylation Pattern

An assay was performed to examine whether the IDS of the present invention is glycosylated and to identify the glycosylation pattern if any. To this end, IDS was treated with various glycoside hydrolase enzymes, the digests were separated on by SDS-PAGE and their motility patterns were analyzed.

In detail, IDS samples were digested with combinations of the following four glycoside hydrolase enzymes and separated by SDS-PAGE.

TABLE 1

Properties of Sugar Cleaving Enzymes

| | Function/Property |
|---|---|
| PNGase F | Cleaves a sugar moiety (N-glycan) from protein |
| | Asn at the cleavage site is converted into Asp |
| Endo H | Cleaves a sugar moiety (N-glycan) from protein |
| | unlike PNGase F, Endo H acts on oligosaccharides of high-mannose type and hybrid type |
| O-Glycosidase | Cleaves a sugar moiety (O-glycan) from protein |
| Sialidase | Cleaves terminal sialic acid residues of N-glycan or O-glycan |

Figure 11:
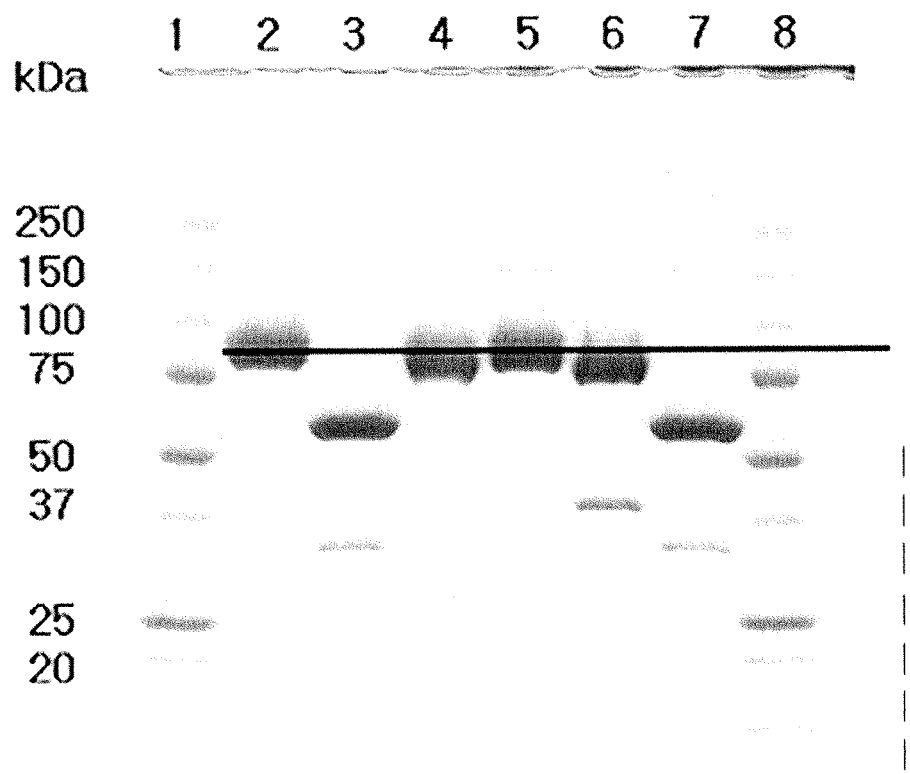
FIG. 11 is a photograph showing IDS run by SDS-PAGE after treatment with various glycoside hydrolase enzymes to examine the glycosylation of the IDS of the present invention.

As can be seen in FIG. 11, the IDS of the present invention was cleaved by PNGase F and Endo H, but not by O-glycosidase, indicating that the IDS of the present invention is an N-glycosylated protein. In addition, the IDS was completely cleaved by PNGase F, but its size reduction was slight upon treatment with Endo H. PNGase F acts on the glycosylation sites of all the three patterns whereas Endo H acts on the glycosylation sites of high-mannose type and hybrid type. Taken together, these results indicate that the IDS contains the three glycosylation patterns complex, high-mannose and hybrid.

<1-5> Analysis of Mannose-6-Phosphate Content

Binding to a M6P receptor on cells, mannose-6-phosphate (M6P) allows IDS to be internalized into cells and thus to hydrolyze heparan sulfate or dermatan sulfate in lysosomes. In this Example, IDS was acid hydrolyzed with trifluoroacetic acid (TFA) and subjected to HPAEC-PAD (Bio-LC) to quantitatively analyze mannose-6-phosphate.

Figure 12:
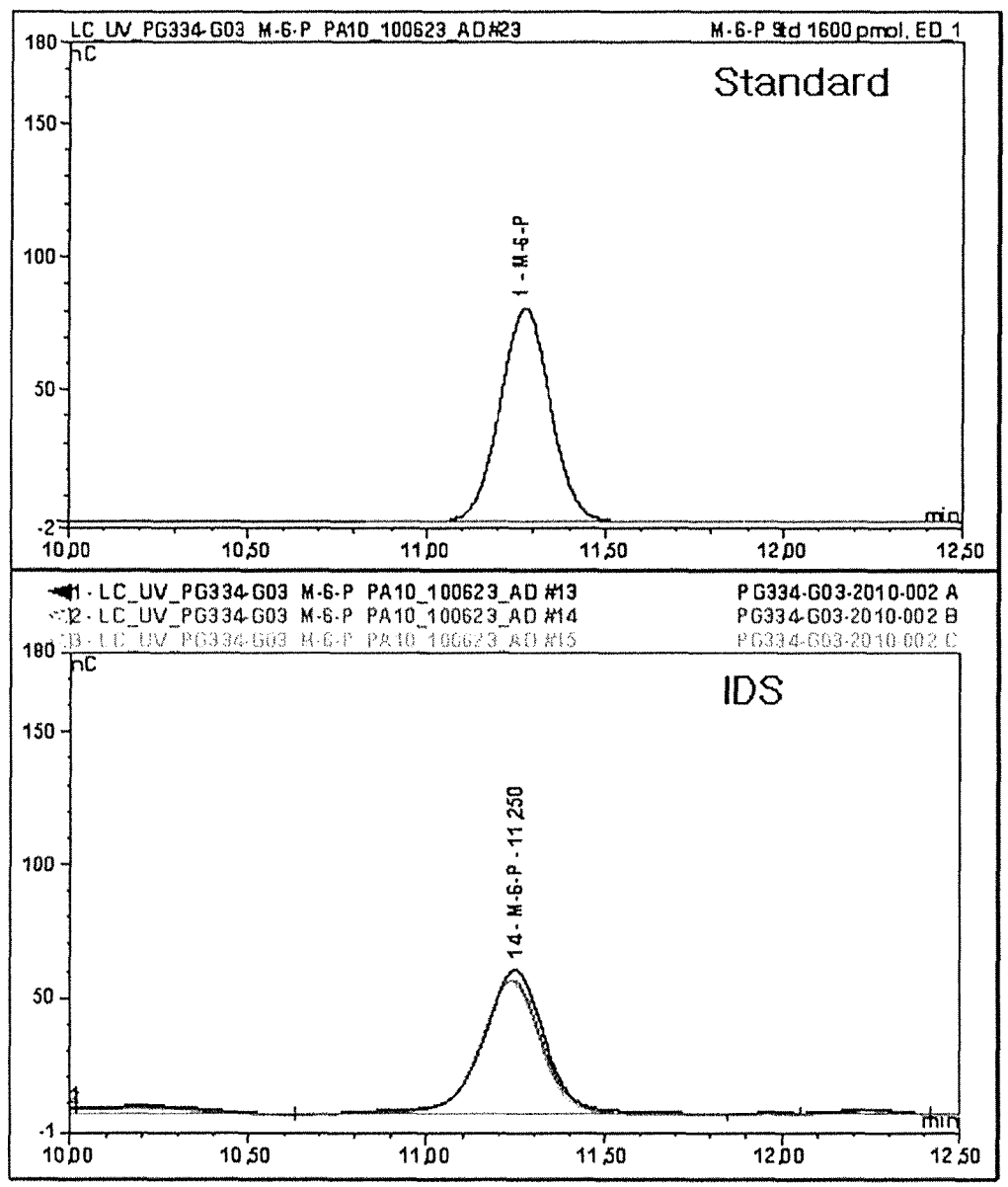
FIG. 12 is of HPAEC-PAD chromatograms showing the content of mannose-6-phosphate in the IDS of the present invention.

IDS was hydrolyzed with 6.75M TFA and the hydrolysate was analyzed using liquid chromatography (High Performance Anion-Exchange Chromatography with Pulsed Amperometric Detection; HPAEC-PAD). M6P concentration of which was already known was analyzed under the same condition, and molar ratios of M6P to glycoprotein were obtained by comparison of the areas. Analysis was conducted in triplicate. M6P standard materials and M6P composition chromatograms of the IDS are shown in FIG. 12 and the molar ratios of M6P are summarized in Table 2, below.

TABLE 2

Analysis Results for Mannose-6-phosphate Content

| Run No. | M-6-P Ret. Time (min) | Amount pmol/25 μl M-6-P | Amount pmol/25 μl Protein | Ratio M-6-P/Protein (mol/mol) |
|---|---|---|---|---|
| 13 | 11.25 | 1320.59 | 428 | 3.09 |
| 14 | 11.23 | 1241.31 | 428 | 2.90 |
| 15 | 11.23 | 1245.83 | 428 | 2.91 |
| AVG | 11.24 | 1269.25 | 428 | 2.97 |
| CV | 0.09% | 3.51% | | 0.11 |

As is understood from the data of Table 2, there are approximately 3 moles of M6P per mole of IDS. From these results, it is inferred that the therapeutic composition comprising the IDS of the present invention and the formulation prepared with the composition have a high ability to catabolize GAG accumulated in lysosomes.

<1-6> Mass Analysis

Masses of glycosylated IDS and deglycosylated IDS were measured using MALDI-TOF-MS. Treatment of glycosylated IDS with PNGase F afforded deglycosylated IDS. MALDI-TOF-MS was performed using Voyager-DE PRO Biospectrometry (Applied Biosystems, USA) coupled with a delayed Extraction laser-desorption mass spectrometer. The instrument was normalized with bovine serum albumin and IgG1. Analysis results are summarized in Table 3, below.

TABLE 3

MALDI-TOF-MSMALDI-TOF-MS Analysis Results of IDS

| m/z | charge(z) | Protein Mass(Da) | remark |
|---|---|---|---|
| Glycosylated IDS | | | |
| 25646 | 3 | 76935 | |
| 38708 | 2 | 77414 | |
| 77360 | 1 | 77359 | |
| 154533 | 1 | 77266 | dimer |
| Average | | 77244 ± 210 | |
| Deglycosylated IDS | | | |
| 29767 | 2 | 59532 | |
| 34655 | | | PNGase F |
| 59313 | 1 | 59312 | |
| 118706 | 1 | 59353 | dimer |
| Average | | 59399 ± 120 | |

| Sample | Molecular Weight |
|---|---|
| Theoretical | 59298 Da |
| Glycosylated | 77244 ± 210 Da |
| Deglycosylated | 59399 ± 120 Da |

As apparent from the data of Table 3, the molecular size is 77,244 Da for glycosylated IDS and 59,399 Da for deglycosylated IDS, which is similar to the molecular weight calculated on the basis of the amino acid sequence, which is 59,298 Da.

<1-7> Purity Measurement

The purity of IDS was measured using size exclusion chromatography. Size exclusion chromatography is a chromatographic method in which molecules in solution are separated by their relative molecular weight and shape. In size exclusion chromatography, proteins larger than the pore size of the column cannot penetrate the pore system and pass through the column at once. Subsequently, the analytes with smaller molecular weights or sizes elute later. For this chromatography, Alliance 2695 HPLC system (Waters, WI, USA) coupled with 2487 UV/VIS detector (Waters, WI, USA) was employed. Proteins were detected at 214 nm, and analyzed using Empower 2 Software. The analytes were loaded onto a TSK G3000SWXL column linked to a TSK SWXL guard column (Tosoh, Japan). IDS, after being diluted to a concentration of 1.0 mg/mL in a formulation buffer, was loaded in a volume of 10 μL onto the column. They were allowed to flow with mobile phase (20 mM sodium phosphate buffer, 200 mM NaCl, pH 7.0) at a flow rate of 0.5 mL/min for 60 min.

Figure 13:
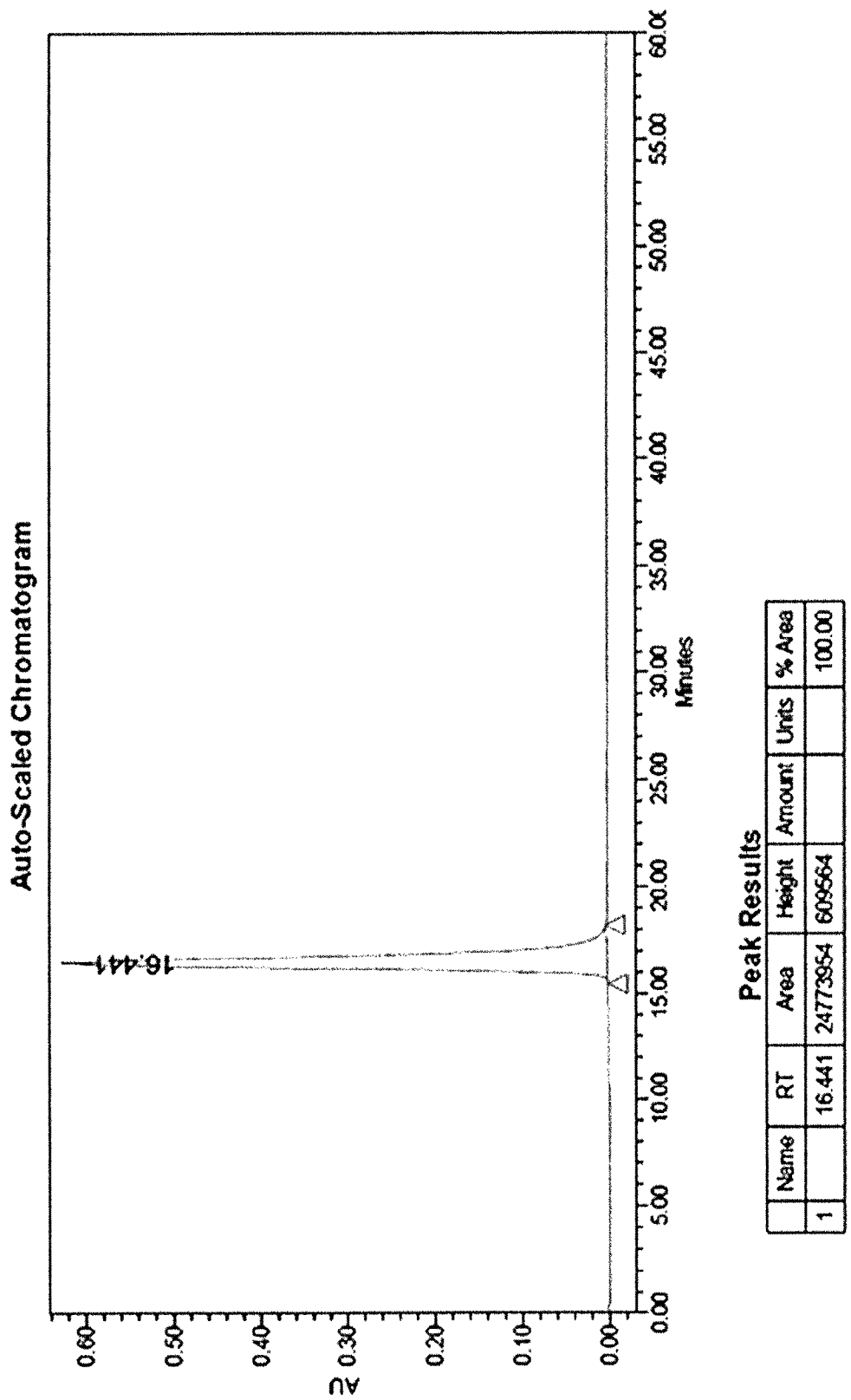
FIG. 13 is a size exclusion chromatogram showing the purity of the IDS of the present invention.

Analysis results are shown in FIG. 13. As can be seen, IDS monomers had a retention time of approximately 16.4 min, and were eluted with 100% purity.

<1-8> Activity Measurement Using Synthetic Substrate

The reaction of IDS with the synthetic substrate (4-methylumbelliferyl-L-iduronide-2-sulfate $Na_2$ (MU-IdoA-2S) for 4 hours releases the sulfate moiety (primary reaction). After the primary reaction, the addition of LEBT (lysosomal enzymes purified from bovine testes) induces a secondary enzymatic reaction with the substrate 4-methylumbellifery-L-iduronide (reactant left after the release of the sulfate moiety in the primary reaction) to separate the 4-methylumbelliferyl moiety from the L-iduronide moiety. Because the remaining 4-methylumbelliferyl is fluorogenic, the activity of IDS was evaluated by measuring the intensity of fluorescence (Ex. 355 nm/Em. 460 nm). The IDS of the present invention was found to range in specific activity from 19 to 55 nmol/min/μg. This activity indicates that formylglycine exists in the active site of the enzyme as a result of the post-translational modification of the cysteine residue at position 59 in IDS.

<1-9> Activity Measurement Using Natural Substrate

In order to determine whether the reaction with the IDS and natural substrate, the sulfate ions released from the substrate (heparin disaccharide) by reaction with IDS were measured. The reaction mixture was loaded onto an ion column (Vydac 302IC) and allowed to flow with the mobile phase of 0.49 g/L phthalic acid at a flow rate of 2 ml/min, during which free sulfate ions were detected at 290 nm in negative mode.

Figure 14:
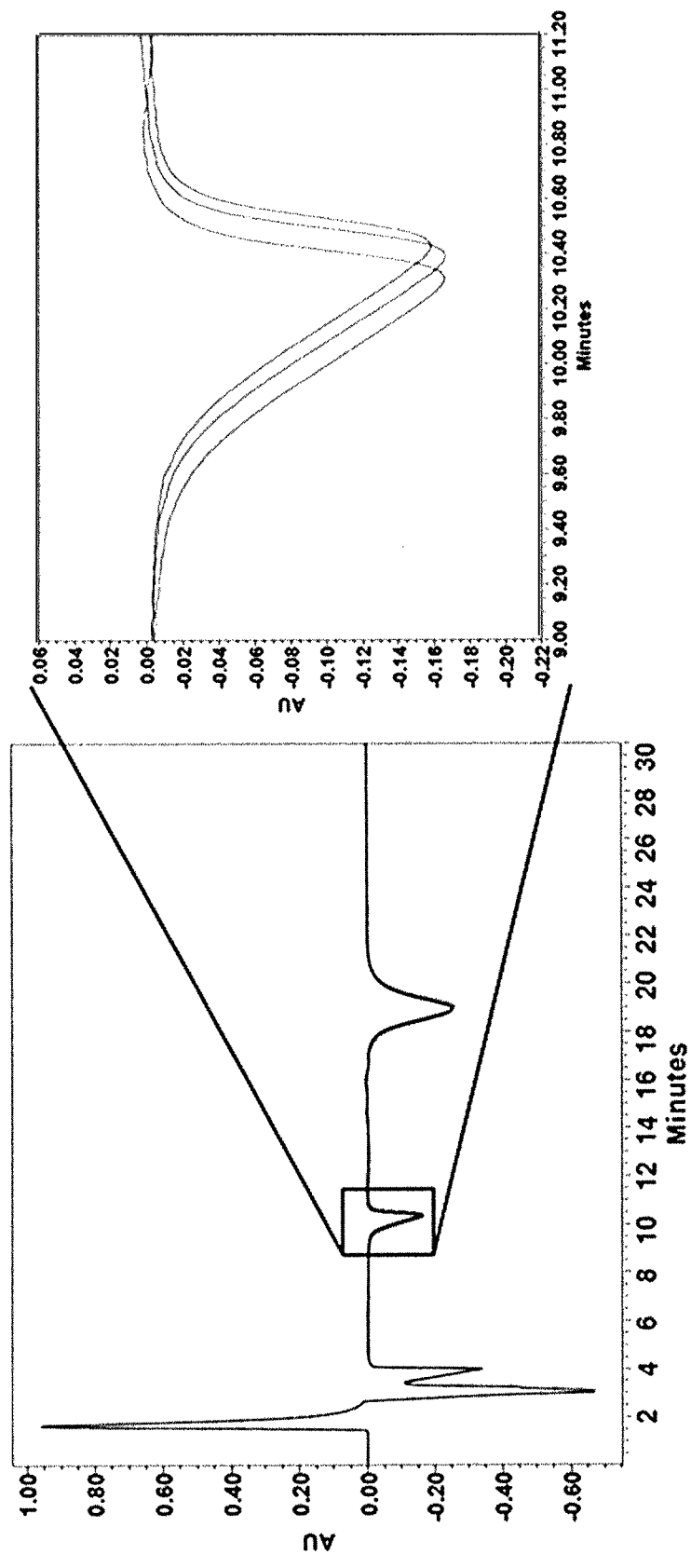
FIG. 14 is an ion chromatogram showing the catalytic activity of the IDS of the present invention on a natural substrate.

As shown in FIG. 14, the IDS was confirmed to hydrolyze sulfate ion from heparin disaccharide, indicating that the IDS is capable of degrading O-linked sulfate of dermatan sulfate and heparan sulfate in vivo.

<1-10> In Vivo Cellular Uptake Activity

The cellular internalization activity of the IDS was measured using the normal fibroblast cells and Hunter syndrome patient cells. In this regard, normal fibroblast cells and Hunter syndrome patient cells (obtained from Samsung Medical Center, Seoul, Korea) were cultured and allowed to be internalized into cells while they were incubated with various concentrations of IDS at 37° C. for 20 hours in a 5% $CO_2$ incubator. After being harvested, the cells were lyzed, and the level of the IDS internalized into the cells was determined in the lysate.

Figure 15:
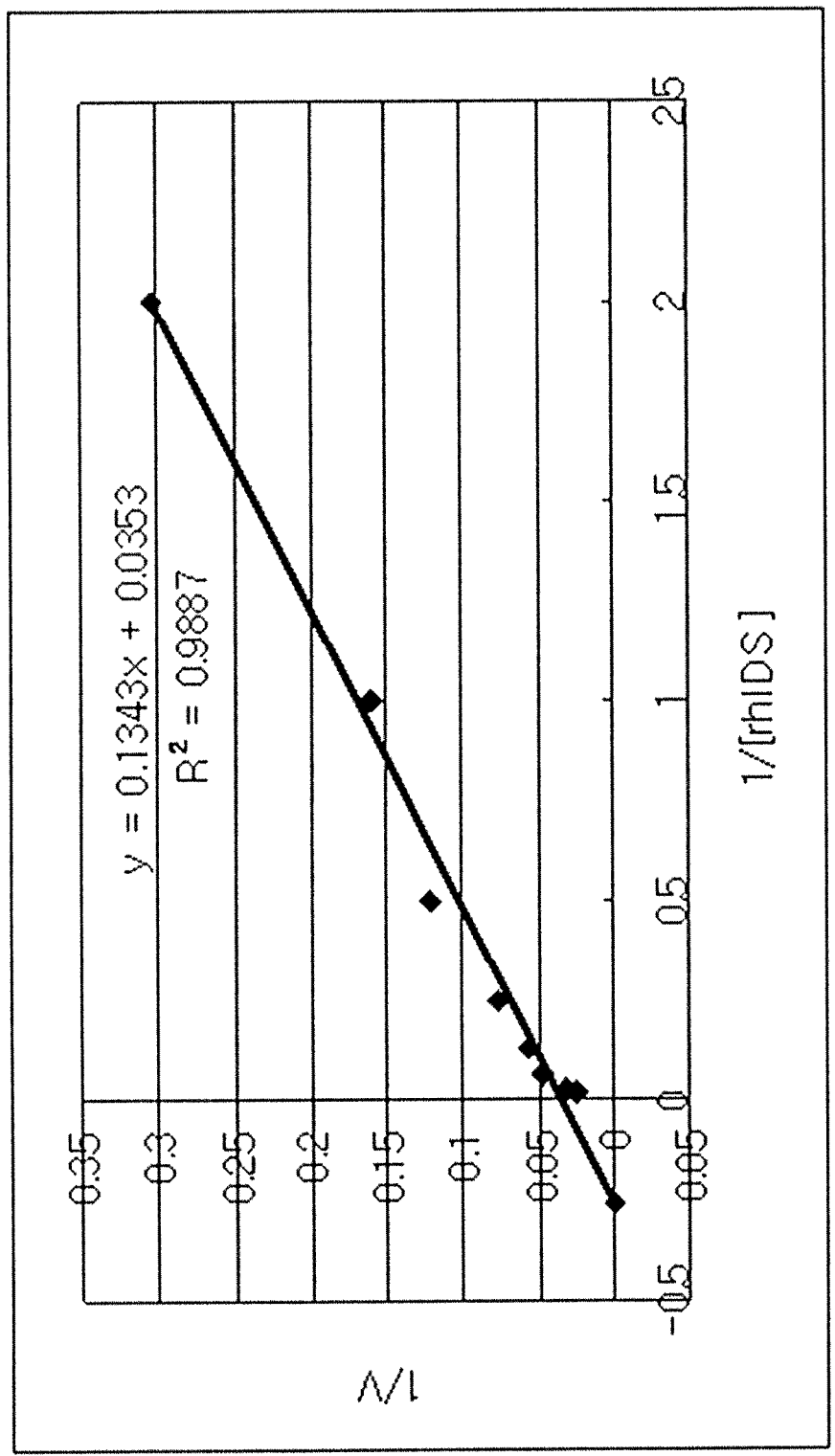
FIG. 15 is Lineweaver-Burk plot showing ratios of cellular uptake amounts of IDS relative to amount of IDS added to normal fibroblast cells.

On the basis of the concentration ratio of internalized IDS to IDS added to the normal fibroblast cells, a Michaelis-Menten graph and a Lineweaver-Burk plot were constructed from which $K_{uptake}$ (IDS concentration at which the reaction rate is half of the maximum rate achieved at saturating substrate concentrations) was calculated. $K_{uptake}$ was calculated to be 18.0 nM or less, indicating that IDS is internalized into cells by the binding of the M6P of IDS to M6P receptors on the cell surface (FIG. 15).

Figure 16:
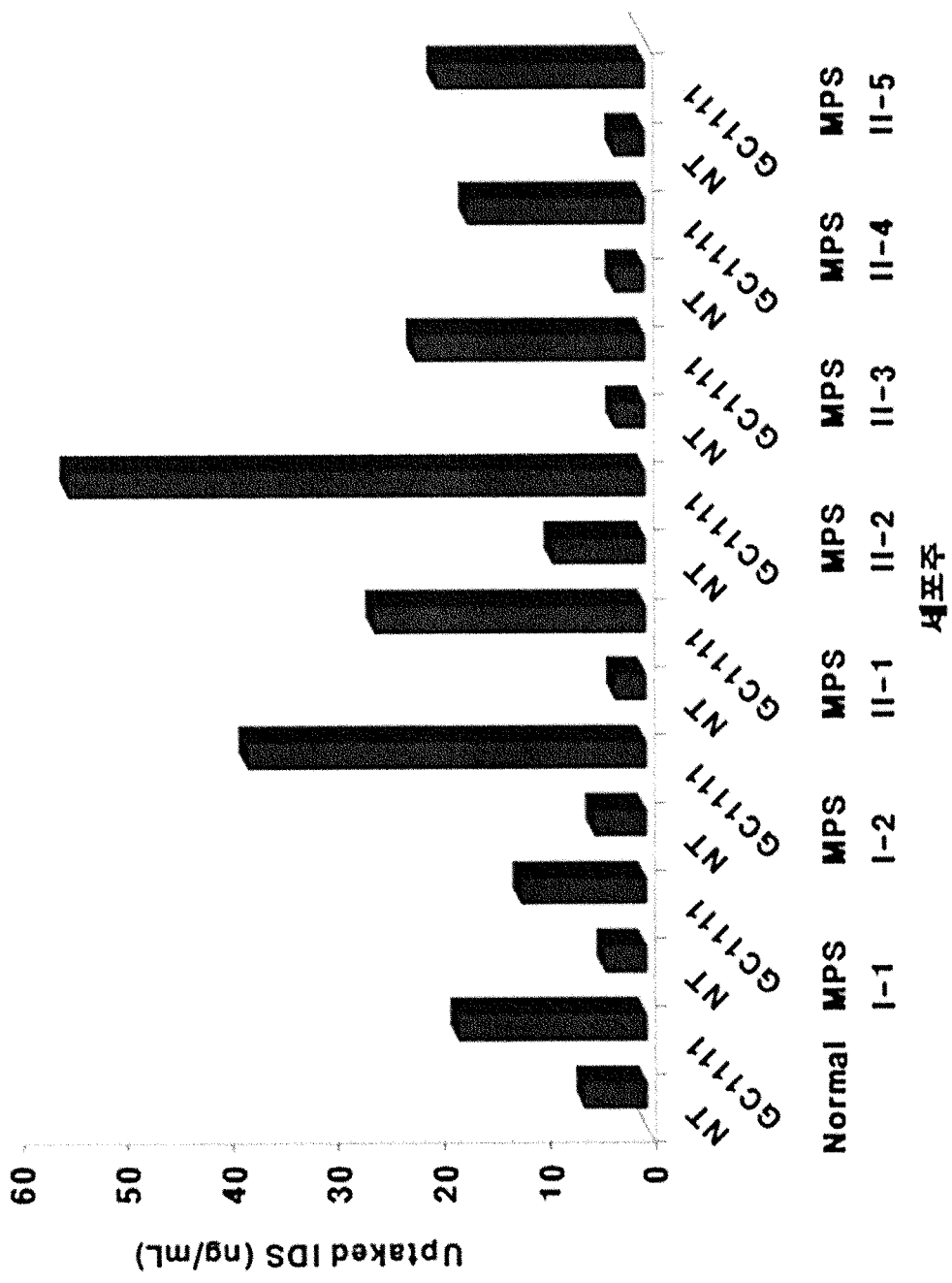
FIG. 16 is a graph showing the amount of the IDS of the present invention internalized into normal human fibroblast cells and the cells of patients suffering from Hunter syndrome.
Figure 17:
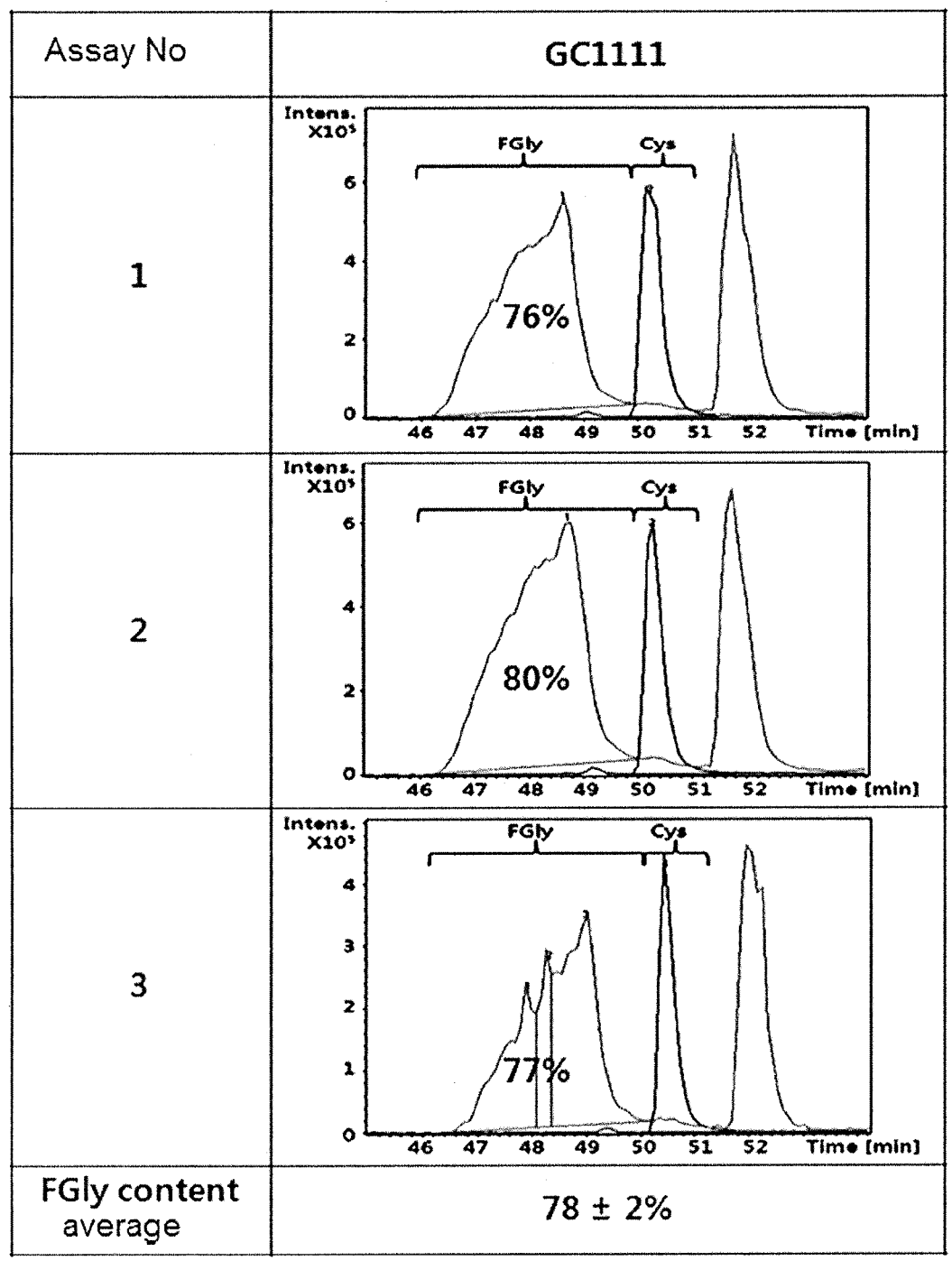
FIG. 17 is a view showing measurements of the formylglycine content in the IDS of the present invention.
Figure 18:
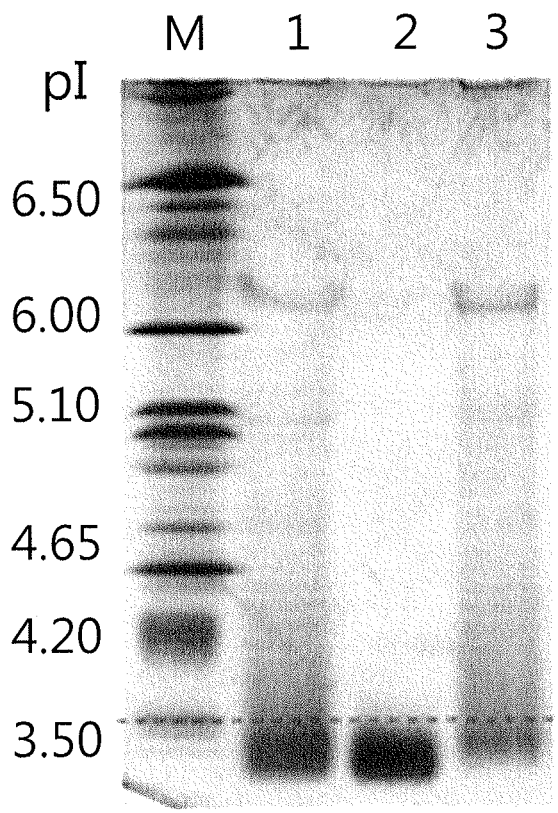
FIG. 18 is a view showing IEF (isoelectric focusing) points of the IDS of the present invention before and after cation exchange chromatography wherein M is run on M lane, a loaded sample for cation exchange chromatography on lane 1, an eluate of cation exchange chromatography on lane 2, and a regeneration solution after cation exchange chromatography on lane 3.

Also, the cellular uptake and activity of IDS in Hunter syndrome patient cells as well as normal human fibroblast cells were analyzed. The uptake and activity of the IDS were increased in both the cells, demonstrating that the IDS of the present invention is more efficiently internalized into cells (FIG. 16).

Experimental Example 2

Clinical Analysis for Effect of IDS

Thirty one patients with Hunter syndrome were divided into three groups, administered with the IDS of the present invention and analyzed for parameters associated with Hunter syndrome. Elaprase®, a commercially available therapeutic agent for Hunter syndrome, was used as a positive control.

<2-1> Change in Urine GAG Level (Primary Check Parameter for Validity Test)

The three groups of Hunter syndrome patients were administered for 24 weeks with Elaprase (0.5 mg/kg) and the IDS of the present invention (0.5 mg/kg and 1.0 mg/kg), and urine GAG (Glycosaminoglycan) levels were measured as reported previously (Conn. Tissue Res. Vol. 28, pp 317-324, 1990; Ann. Clin. Biochem. Vol. 31, pp 147-152, 1994). Measurements are summarized in Table 4, below.

TABLE 4

Change in Urine GAG Level with IDS Administration

| Group | Elaprase (0.5 mg/kg) | Inventive IDS (0.5 mg/kg) | Inventive IDS (1.0 mg/kg) |
|---|---|---|---|
| Change in urine GAG level (%) | −18.7 | −29.5 | −41.1 |

In Hunter syndrome patients, as shown in Table 4, urine GAG levels were decreased by 18.7% upon the injection of Elaprase, but by 29.5% upon the injection of the IDS of the present invention at the same dose. In addition, when injected at a dose of 1.0 mg/kg, the IDS of the present invention reduced the urine GAG level by as much as 41.1%. These results demonstrate that the IDS of the present invention is effectively therapeutic for Hunter syndrome, a disease caused as a result of the accumulation of GAG.

<2-2> 6-MWT (6 Minute Walking Test) Change (Secondary Checking Parameter for Validity Test)

After Hunter syndrome patients were administered with Elaprase and the IDS of the present invention for 24 weeks, the distances which they walked for 6 minutes were measured according to the method described in AM. J. Respir. Crit. Care. Med., Vol 166, pp 111-117, 2002. The results are given in Table 5, below.

TABLE 5

6-MWT Test Results

| Group | Elaprase (0.5 mg/kg) | Inventive IDS (0.5 mg/kg) | Inventive IDS (1.0 mg/kg) |
|---|---|---|---|
| 6-MWT Distance (m) | 5.9 | 67.6 | 52.8 |
| 6-MWT Change (%) | 1.3 | 18.2 | 13.4 |

As shown in Table 5, the 6-WMT change was merely 1.3% for the patients administered with Elaprase, but increased to 18.2% for the patients administered with the same dose of the IDS of the present invention. Hunter syndrome patients have trouble walking due to contracture. However, the IDS of the present invention improves the symptoms and thus is effective for the treatment of Hunter syndrome.

The invention claimed is:

1. A composition comprising, as an active ingredient, an iduronate-2-sulfatase (IDS) having the amino acid sequence of SEQ ID NO: 1, wherein a cysteine residue at position 59 in the IDS amino acid sequence is converted into formylglycine (FGly) at a molar ratio of 65% or higher.

2. The composition of claim 1, wherein the cysteine residue at position 59 in the IDS amino acid sequence is converted into FGly at a molar ratio of 75% or higher.

3. The composition of claim 1, wherein the IDS contains mannose-6-phosphate in an amount of 2.0 to 4.0 moles per mole of IDS.

4. The composition of claim 3, wherein the IDS contains mannose-6-phosphate in an amount of 2.5 to 3.0 moles per mole of IDS.

5. A formulation comprising the composition of claim 1.

6. The formulation of claim 5, further comprising:
a pharmaceutically acceptable carrier; and
a substance selected from the group consisting of a buffer, a carbohydrate, a stabilizer, an antioxidant, a bacteriostatics, a chelating agent, an adjuvant, a suspending agent, a thickener, and a preservative.

7. A method for preparing the composition of claim 1, comprising:
(1) culturing a recombinant host cell strain transformed with a gene encoding IDS comprising the amino acid sequence of SEQ ID NO: 1 and obtaining the culture; and
(2) purifying the IDS from the culture through anion exchange chromatography, hydrophobic chromatography, cation exchange chromatography, and affinity chromatography to obtain the composition.

8. A method for preparing the composition of claim 1, comprising:
(1) transforming a host cell with an expression vector carrying an IDS gene to obtain a recombinant cell strain;
(2) culturing the recombinant cell strain in the presence of a hydrolysate in a serum-free medium and obtaining the culture;
(3) purifying the IDS from the culture through anion exchange chromatography, hydrophobic chromatography, cation exchange chromatography and affinity chromatography; and
(4) combining the purified IDS with a pharmaceutically acceptable carrier to obtain the composition.

9. The method of claim 7, wherein the host cell is a Chinese hamster ovary cell.

10. The method of claim 7, wherein the cation exchange chromatography is performed using an elution buffer with a pH of 4.0 to 6.0.

11. The method of claim 7, wherein the hydrophobic chromatography is performed using an elution buffer with a pH of 5.0 to 7.0.

12. The method of claim 7, wherein the affinity chromatography is performed using an elution buffer with a pH of 6.0 to 8.0.

13. The method of claim 7, wherein the anion exchange chromatography is performed using an elution buffer with a pH of 5.5 to 7.5.

14. The method of claim 7, further comprising inactivating viruses at a pH of 3.0 to 4.0.

15. A method for preparing a formulation for treating Hunter syndrome, comprising formulating the composition prepared according to the method of claim 7.

16. The method of claim 8, wherein the host cell is a Chinese hamster ovary cell.

17. The method of claim 8, wherein the cation exchange chromatography is performed using an elution buffer with a pH of 4.0 to 6.0.

18. The method of claim 8, wherein the hydrophobic chromatography is performed using an elution buffer with a pH of 5.0 to 7.0.

19. The method of claim 8, wherein the affinity chromatography is performed using an elution buffer with a pH of 6.0 to 8.0.

20. The method of claim 8, wherein the anion exchange chromatography is performed using an elution buffer with a pH of 5.5 to 7.5.

21. The method of claim 8, further comprising inactivating viruses at a pH of 3.0 to 4.0.

22. The formulation of claim 5, wherein the cysteine residue at position 59 in the IDS amino acid sequence is converted into FGly at a molar ratio of 75% or higher.

23. The formulation of claim 5, wherein the IDS contains mannose-6-phosphate in an amount of 2.0 to 4.0 moles per mole of IDS.

24. The formulation of claim 23, wherein the IDS contains mannose-6-phosphate in an amount of 2.5 to 3.0 moles per mole of IDS.

* * * * *